(12) United States Patent
Sahai et al.

(10) Patent No.: US 10,537,317 B2
(45) Date of Patent: Jan. 21, 2020

(54) ANTERIOR CERVICAL DISTRACTOR SYSTEM AND TECHNIQUE

(71) Applicant: Spine Ortho Center, P.A., Deerfield Beach, FL (US)

(72) Inventors: Ashish K. Sahai, Boca Raton, FL (US); Nikhil Sahai, Boca Raton, FL (US)

(*) Notice: Subject to any disclaimer, the term of this patent is extended or adjusted under 35 U.S.C. 154(b) by 425 days.

(21) Appl. No.: 15/291,736

(22) Filed: Oct. 12, 2016

(65) Prior Publication Data

US 2017/0100117 A1   Apr. 13, 2017

Related U.S. Application Data

(60) Provisional application No. 62/240,186, filed on Oct. 12, 2015.

(51) Int. Cl.
| | | |
|---|---|---|
| A61B 17/02 | (2006.01) | |
| A61B 17/70 | (2006.01) | |
| A61B 17/80 | (2006.01) | |
| A61B 17/68 | (2006.01) | |

(52) U.S. Cl.
CPC ........ *A61B 17/025* (2013.01); *A61B 17/7059* (2013.01); *A61B 17/8019* (2013.01); *A61B 2017/0256* (2013.01); *A61B 2017/681* (2013.01)

(58) Field of Classification Search
CPC ..................... A61B 17/025; A61B 2017/0256
See application file for complete search history.

(56) References Cited

U.S. PATENT DOCUMENTS

| | | | |
|---|---|---|---|
| 7,494,463 B2* | 2/2009 | Nehls | A61B 17/0206 600/227 |
| 8,936,599 B2* | 1/2015 | Glazer | A61B 17/7077 606/105 |

* cited by examiner

*Primary Examiner* — Andrew Yang
(74) *Attorney, Agent, or Firm* — McHale & Slavin, P.A.

(57) ABSTRACT

An Anterior Cervical Distractor System and Technique of use for surgical procedures to correct cervical spinal deformities is described. The Anterior Cervical Distractor System includes a cervical distractor having a distracting assembly for distracting vertebral bodies and a centering assembly for providing proper alignment. A plurality of control knobs, a distractor assembly control knob and a centering component assembly control knob, are used to allow the surgeon to control the centering and distracting functionality.

18 Claims, 27 Drawing Sheets

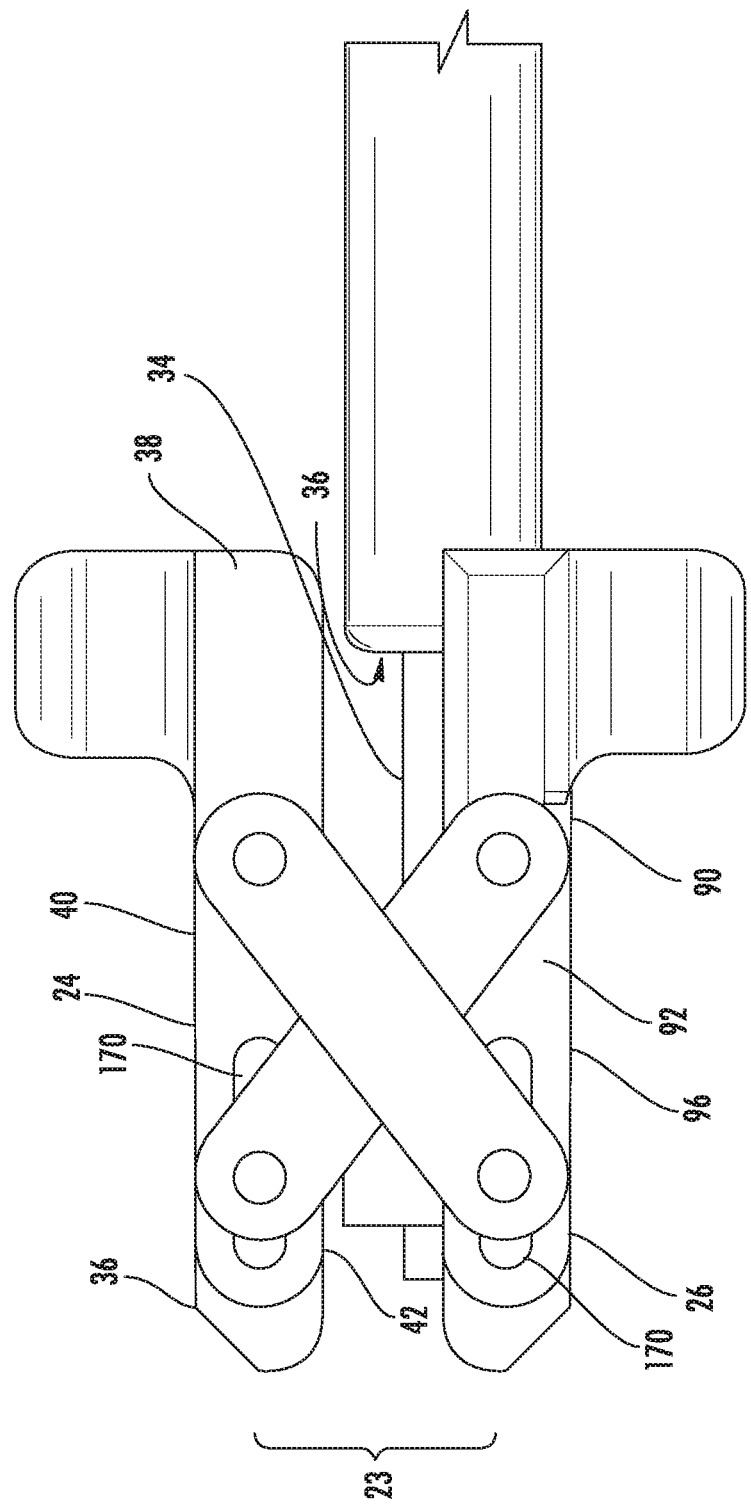

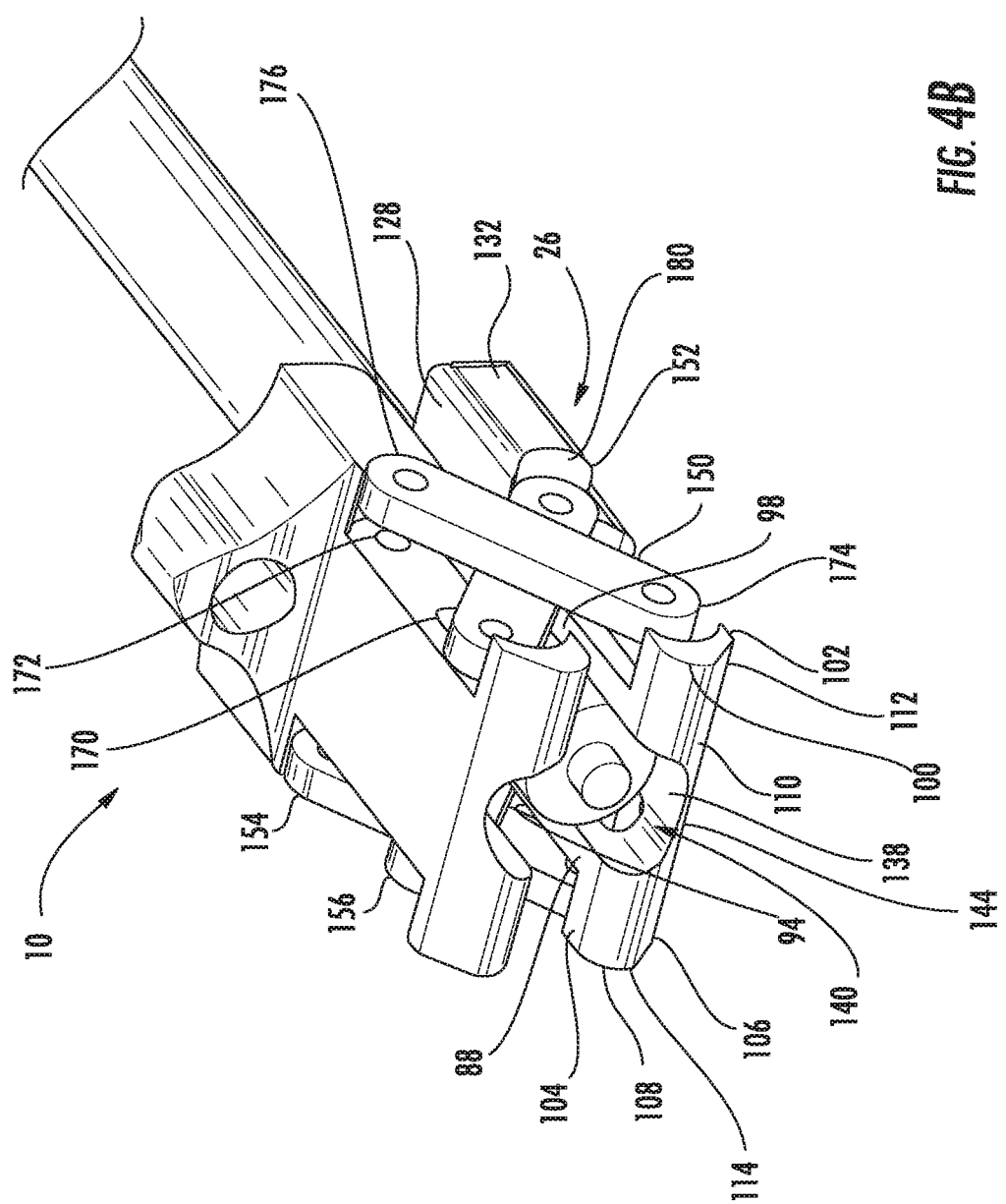

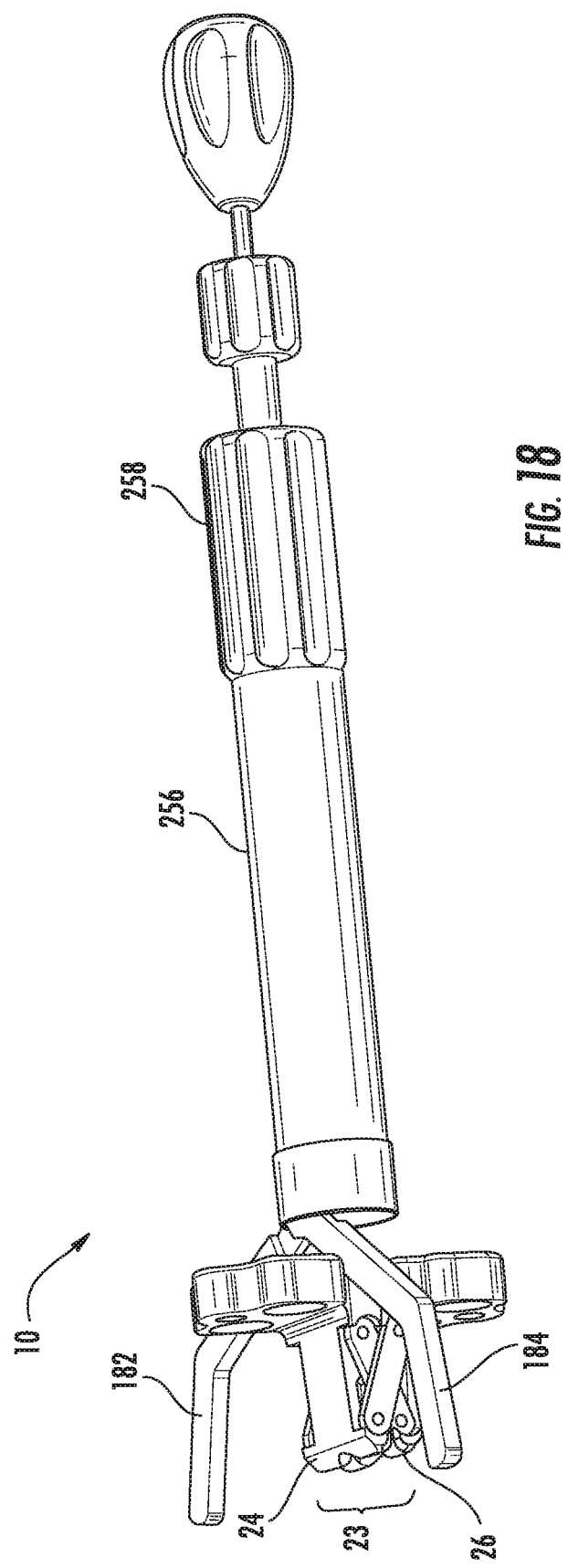

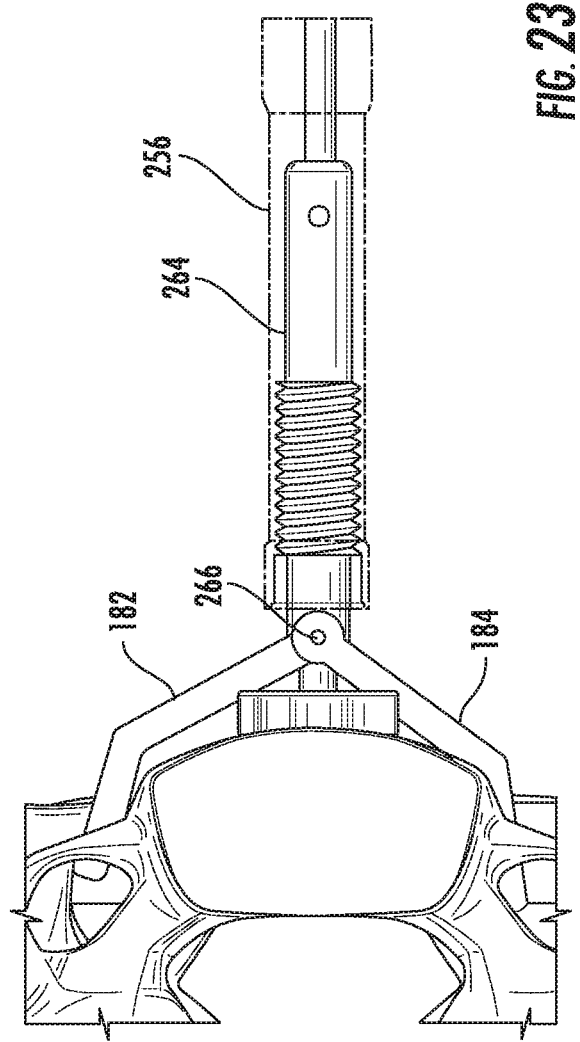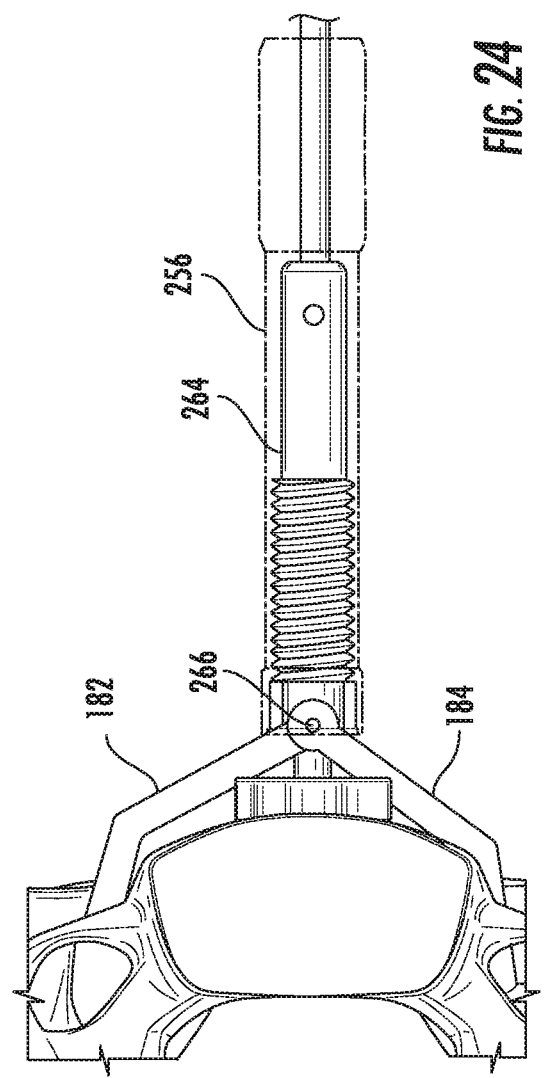

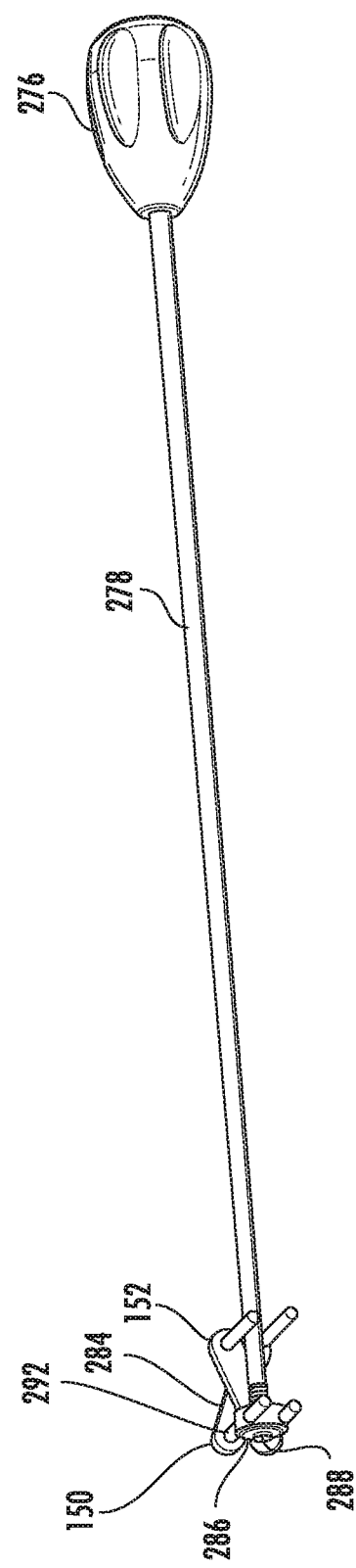

ANTERIOR CERVICAL DISTRACTOR SYSTEM AND TECHNIQUE

CROSS-REFERENCE TO RELATED APPLICATION

In accordance with 37 C.F.R. 1.76, a claim of priority is included in an Application Data Sheet filed concurrently herewith. Accordingly, the present invention claims priority to U.S. Provisional Patent Application No. 62/240,186, entitled "ANTERIOR CERVICAL DISTRACTOR SYSTEM AND TECHNIQUE", filed Oct. 12, 2015. The contents of the above referenced application is incorporated herein by reference in its entirety.

FIELD OF THE INVENTION

The present invention relates to instruments and methods for use with spinal surgeries. More specifically, the present invention relates to an Anterior Cervical Distractor System and Technique for use in surgical procedures to correct cervical spinal deformities.

BACKGROUND OF THE INVENTION

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints, allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the anulus fibrosus ("anulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae. The anulus of the disc forms the disc perimeter, and is a tough, outer fibrous ring that binds adjacent vertebrae together. The fibrous layers of the anulus include fifteen to twenty overlapping plies, which are inserted into the superior and inferior vertebral bodies at roughly a 40-degree angle in both directions. This causes bi-directional torsional resistance, as about half of the angulated fibers will tighten when the vertebrae rotate in either direction. It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance.

Age related wear and tear affecting the spinal discs in the neck affects many individuals. Impaired function of the spinal cord, resulting from degenerative changes of the discs or facet joints in the cervical spine, can be painful. The condition seems to worsen with age. While the condition can be treated with medication to alleviate the pain, if symptoms or neurological signs get worse, surgical intervention is usually required. Surgical procedures may require the damaged disc to be removed and be replaced with a disc prosthesis intended to duplicate the function of the natural spinal disc. In other cases it is desired to fuse the adjacent vertebrae together after removal of the disc, sometimes referred to as "intervertebral fusion" or "interbody fusion."

SUMMARY OF THE INVENTION

The present invention relates to an Anterior Cervical Distractor System and Technique of use for surgical procedures to correct cervical spinal deformities. The Anterior Cervical Distractor System includes a cervical distractor having a distracting assembly for distracting vertebral bodies, and a centering assembly for providing proper alignment. A plurality of control knobs, a distractor assembly control knob and a centering component assembly control knob, are used to allow the surgeon to control the centering and distracting functionality.

In one example, the distractor device comprises an elongated body having a first end and a second opposing end; a plurality of distraction members positioned at or near the first end; a pair of positioning members configured to aid in positioning said elongated body in place; a first actuating mechanism configured to actuate said pair of distracting members between a first closed position and a second distracted position; and a second actuating mechanism configured to actuate said pair of positioning members between a first retracted and non-retracted position.

In an alternative embodiment, the distractor device may comprise a distraction assembly comprising an elongated body having a first end and a second opposing end, a plurality of distraction members positioned at or near the first end; said plurality of distraction members including at least one first distracting member arranged and one second distracting member, said first distracting member and said second distracting member configured to engage with portions of adjacent vertebral bodies in a closed, non-distraction position, and when separated in an open, distracted position, provide a mechanism to move one vertebral body relative to the other adjacent vertebral body; and a distraction assembly actuating mechanism configured to actuate said distracting members between a first closed position and a second distracted position; and a centering component assembly comprising a first positioning member configured to aid in positioning said elongated body in place and a second positioning member configured to aid in positioning said elongated body in place, and a centering component assembly actuating mechanism configured to actuate said first positioning member and said second positioning member between a retracted and non-retracted position.

Accordingly, it is an objective of the present invention to provide an Anterior Cervical Distractor System and Technique of use for surgical procedures to correct cervical spinal deformities.

It is a further objective of the present invention to provide an Anterior Cervical Distractor System and Technique of use for surgical procedures to correct cervical spinal deformities utilizing a cervical distractor having a distractor assembly.

It is yet another objective of the present invention to provide an Anterior Cervical Distractor System and Technique of use for surgical procedures to correct cervical spinal deformities utilizing a cervical distractor having a centering assembly for centering against the Uncinate Process.

It is a still further objective of the invention to provide an Anterior Cervical Distractor System and Technique of use for surgical procedures to correct cervical spinal deformities utilizing a cervical distractor having a distractor assembly designed to have similar geometry as a cage or trial.

It is yet another objective of the present invention to provide an Anterior Cervical Distractor System and Technique of use for surgical procedures to correct cervical spinal deformities utilizing a cervical distractor having a distractor assembly, a centering assembly for centering against the Uncinate Process, and a fixed cervical plate.

It is another objective of the present invention to provide an Anterior Cervical Distractor System and Technique of use for surgical procedures to correct cervical spinal deformities utilizing a cervical distractor having a distractor assembly, a centering assembly for centering against the Uncinate Process, and a dynamic cervical plate.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 3 is a side view of the cervical distractor illustrated with several components of the centering component assembly omitted for clarity;

FIG. 4B is a perspective view of the cervical distractor illustrated in FIG. 1 without several components of the centering component assembly;

FIG. 18 is an alternative perspective view of the cervical distractor in accordance with the present invention;

FIG. 23 illustrates the outer tube shaft, shown in a transparent view, in the open position;

FIG. 24 illustrates the outer tube shaft, shown in a transparent view in a closed position;

FIG. 29 is an additional view of the central rod illustrated in FIG. 28, shown engaged with components of the distractor assembly.

DETAILED DESCRIPTION OF THE INVENTION

Figure 1:
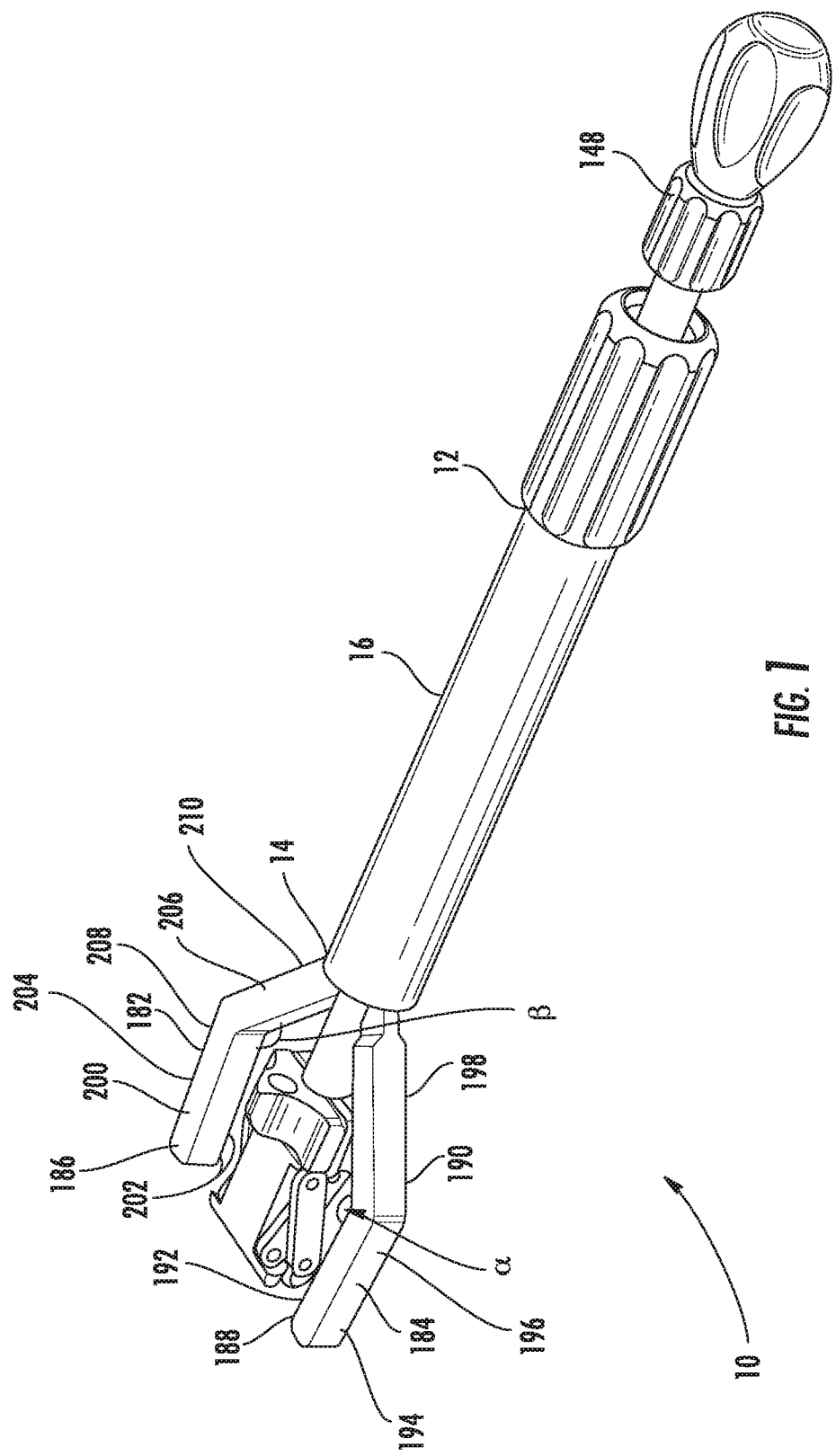
FIG. 1 is a perspective view of an illustrative embodiment of a cervical distractor in a closed orientation.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 2:
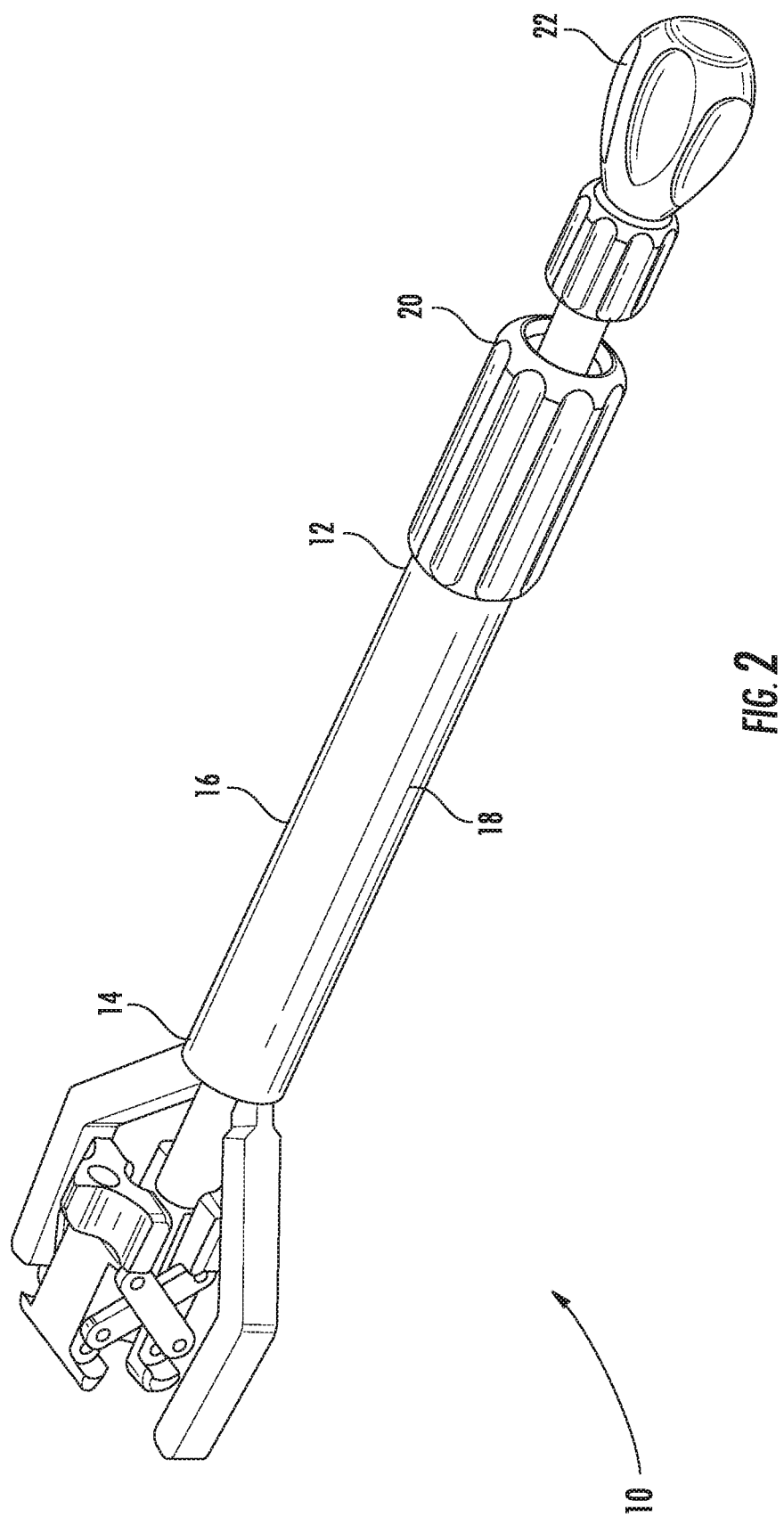
FIG. 2 is a perspective view of the cervical distractor illustrated in FIG. 1 in an open, distracting orientation.

The present invention is directed towards instruments and/or a system for use in surgical procedures to correct cervical spinal deformities. Referring to FIGS. 1 and 2, an illustrative embodiment of a cervical distractor, referred to generally as 10, is shown. The cervical distractor 10 includes a first proximal end 12 defined as the end closest to the surgeon when in use, a second distal end 14 defined as the end closest to the spine and furthest from the surgeon when in use, a longitudinal axis 15, and an elongated main body 16 there between. The elongated main body 16 comprises a continuous side wall 18 thereby forming a generally cylindrical shape outer sleeve. Positioned within the lumen of the continuous side wall is an inner sleeve 17, illustrated having a generally cylindrical shape. The inner sleeve is sized to extend out past the first end and the second end of the elongated body. Positioned at or along the first proximal end 12 is a plurality of control knobs, including a distractor assembly control knob and centering component assembly control knob 22. The control knobs are operatively coupled or engaged with separate actuating mechanisms to independently manipulate the distraction assembly and the centering component assembly into various positions or configurations.

Referring to FIGS. 3-6, the cervical distractor 10 is shown without a centering component assembly to illustrate the components of the distractor assembly. The cervical distractor 10 contains a distractor assembly, referred to generally as 23. The distractor assembly 23 is designed to provide the necessary components to allow distraction of vertebral bodies of the spine. The distractor assembly 23 comprises a plurality of distraction members, illustrated herein as a first distracting plate 24 and a second distracting plate 26. The distracting plates 24 and 26 are arranged at or about a first end 28 of a distractor rod 30, in a parallel manner. The distractor rod 30 is positioned within the inner lumen 35 of the inner sleeve 17 and connects to the distractor assembly control knob 20 (see FIG. 6) at or along its second end 32. The distractor rod main body 34 is sized and shaped to extend through and move in a linear manner or rotate about the internal hollow lumen 35 (see FIG. 3), with the inner sleeve 17 extending through the inner lumen of the elongated main body 16.

Each of the distracting plates 24 and 26 are constructed and arranged to engage with portions of adjacent cervical vertebral bodies, thereby providing a mechanism to move one vertebral body relative to the other adjacent vertebral body. The distracting plate 24 contains a first end 36 and an opposing second end 38. The first end 36 and the second end 38 are separated by side walls 37 and 39. A generally planar upper surface 40 faces a vertebral body when used in a surgical procedure. An opposing bottom surface 42 faces the distractor rod main body 34. The distracting plate 24 contains a tip 44 designed to provide a similar geometrical shape as a cage or trial. As shown, the first distracting plate tip 44 comprises a first planar surface 46 in the same orientation as the upper surface 40 (i.e. facing the vertebral body) and a second planar surface 48 in the same orientation as the bottom surface, i.e. facing the distractor rod main body 34. A pair of angled surfaces 50 and 52 converges at planar surface 54 to provide for a tapered configuration. The first distracting plate tip 44 also contains wings 56 and 58 which extend out past side walls 37 and 39.

Positioned at the opposing second end 38 is a guide member, illustrated herein as a pin guide member 60. The pin guide member 60 contains an upper surface 62 defined by inwardly curved surfaces 64 and 66 that extend downwardly toward the upper surface 40 from apex 67, and a generally planar bottom surface 68 (not shown). An inwardly directed surface 69, i.e. towards the distracting plate 24, contains curvatures designed to approximate the curvature of a vertebra body, thereby providing support and proper fit when the distracting plate 24 is inserted between two vertebrae bodies. A pair of pin guide member side walls 70 and 72 separate the upper surface 62 and the bottom surface 68. A pin guide 74, defined by opening 76 is sized and shaped to receive a pin, such as a Caspar pin, and provides the surgeon with a mechanism to aid in properly aligning and placing the pin in the correct position.

Positioned along the length of the opposing bottom surface 42 and extending into the distal tip 44 and pin guide member 60 is a first portion of a guide channel 78. The guide channel 78 includes partial openings 80 (located in the distal tip 44) and 82 (located in the pin guide member 60). The openings are defined by the curved surfaces 84 and 86, each having a curvature radius sized to accommodate the distractor rod 30 and/or the main body 16 when inserted therein, thereby allowing the distractor rod 30 and/or the main body 16 to linearly move within while maintaining the proper orientation and direction.

Figure 4A:
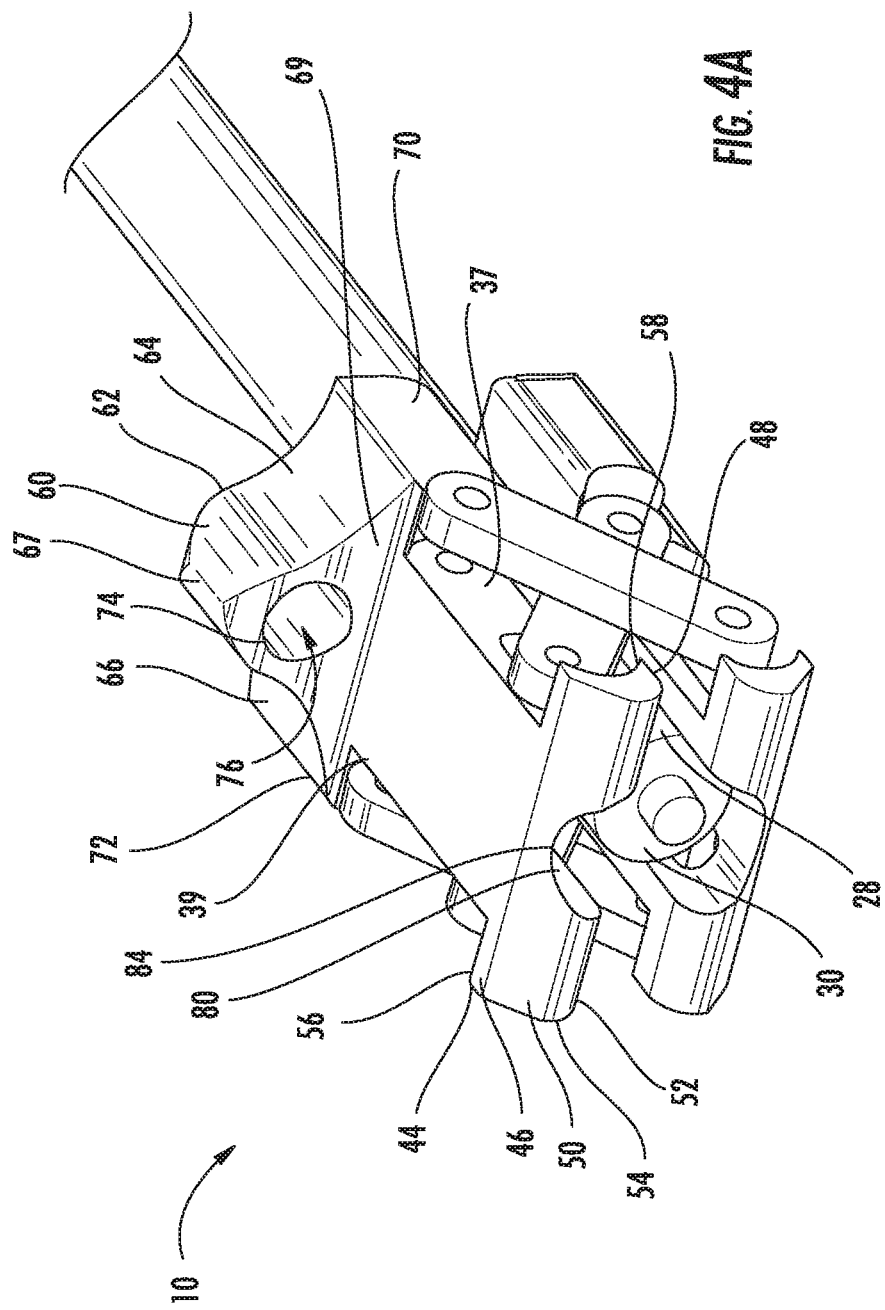
FIG. 4A is a perspective view of the cervical distractor illustrated in FIG. 1 without several components of the centering component assembly.
Figure 4C:
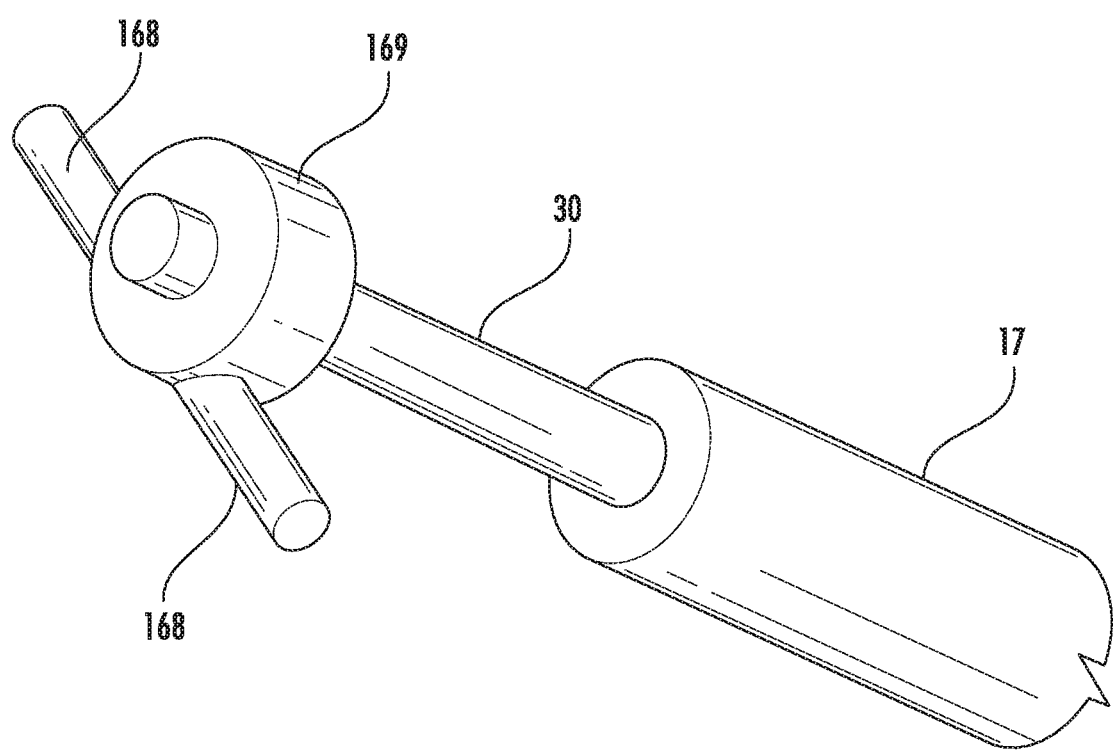
FIG. 4C illustrates a portion of the cervical distractor, illustrating the expansion member pivoting rod cylindrical drive member.

Oppositely arranged about the distractor rod 30 when inserted therein is the second distracting plate 26. The second distracting plate 26 contains a first end 88 and an opposing second end 90. The first end 88 and the second end 90 are separated by side walls 92 and 94 (see FIGS. 3 and 4B). A generally planar upper surface 96 faces a vertebral body when used in a surgical procedure. An opposing bottom surface 98 faces the distractor rod main body 34. The second distracting plate 26 contains a tip 100 designed to provide a similar geometrical shape as a cage or trial. As shown in FIG. 4B, the second distracting plate tip 100 comprises a first planar surface 102 in the same orientation as the upper surface 96 (i.e. facing the vertebral body) and a second planar surface 104 in the same orientation as the bottom surface 98, i.e. facing the distractor rod main body 34. A pair of angled surfaces 106 and 108 converges at planar surface 110 to provide for a tapered configuration. The second distracting plate tip 100 also contains wings 112 and 114 which extend out past side walls 92 and 94.

Figure 5:
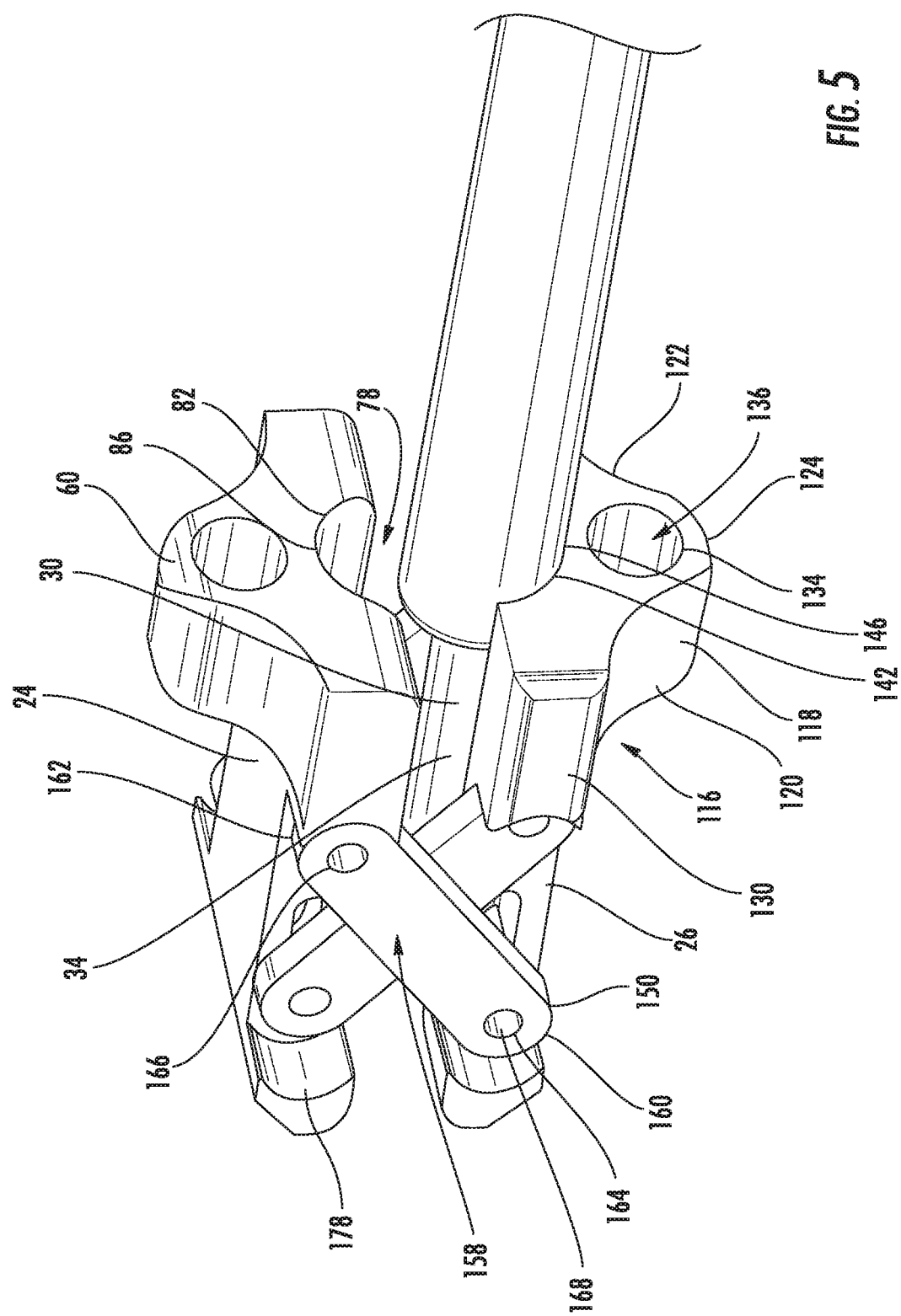
FIG. 5 is an alternative perspective view of the cervical distractor illustrated without several components of the centering component assembly.
Figure 6:
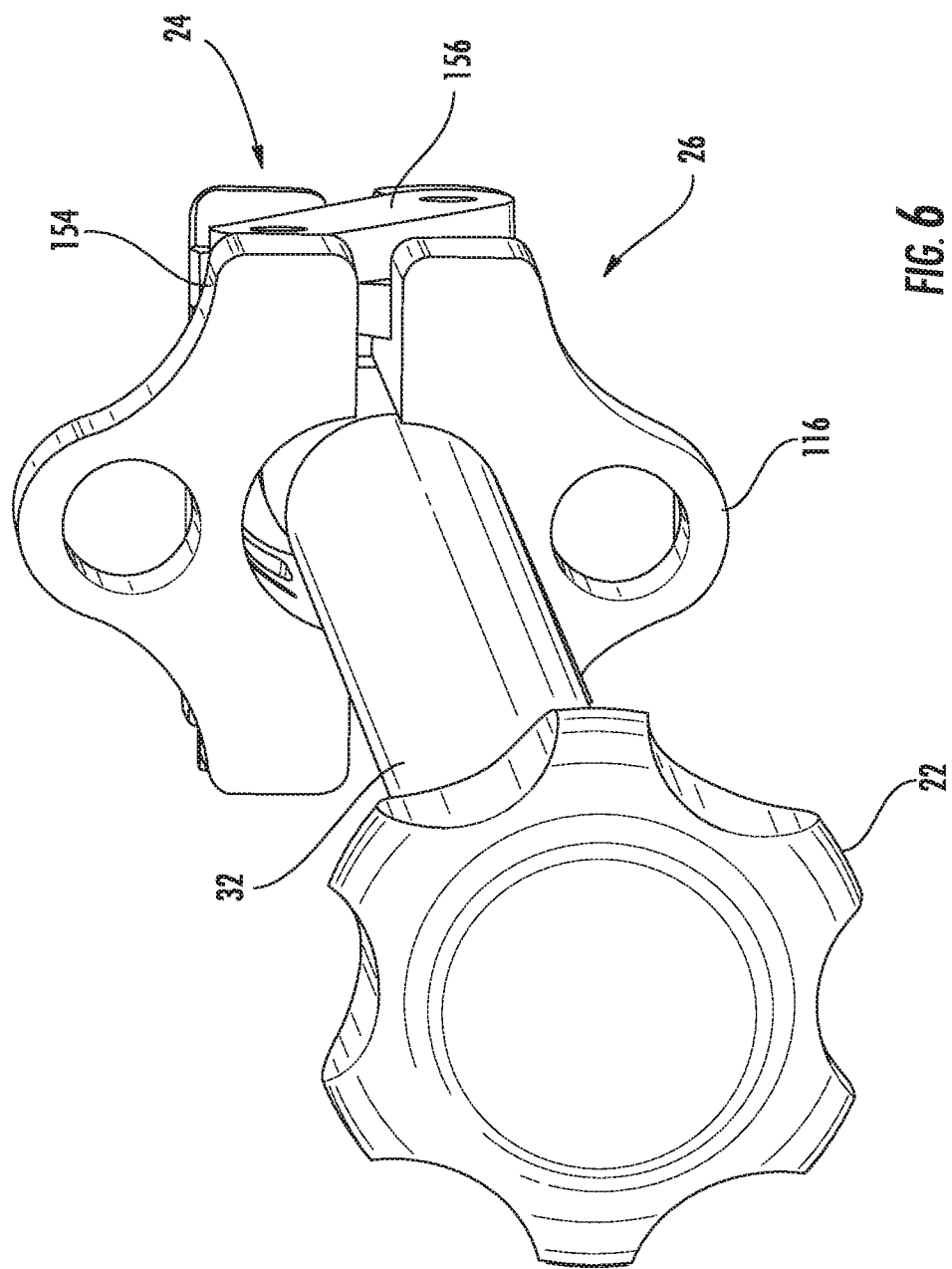
FIG. 6 is a front perspective view of the cervical distractor without several components of the centering component assembly.

Positioned at the opposing second end 90 is a guide member, illustrated as a pin guide member 116 (see FIG. 5). The pin guide member 116 contains an upper surface 118 defined by inwardly curved surfaces 120 and 122 that extend away from upper surface 96, terminating in an apex 124, and a generally planar bottom surface 128. The pin guide member 116 contains an inwardly directed surface 125 (not shown) similar to the surface 69 having curvatures designed to approximate the curvature of a vertebra body, thereby providing support and proper fit when the distracting plate 26 is inserted between two vertebrae bodies. A pair of pin guide member side walls 130 and 132 separate the upper surface 96 and the bottom surface 98. A pin guide 134, defined by opening 136 is sized and shaped to receive a pin, such as a Caspar pin, provides the surgeon with a mechanism to aid in properly aligning and placing the pin in the correct position.

Positioned along the length of the opposing bottom surface 98 and extending into the distal tip 100 and pin guide member 116 is a second member 138 of guide channel 78. The second member 138 of guide channel 78 includes partial openings 140 (located in the distal tip 100) and 142 (located in the pin guide member 116). The openings are defined by the curved surfaces 144 and 146, each having a curvature radius sized to accommodate the distractor rod 30 when inserted therein, thereby allowing the distractor rod 30 to linearly move within while maintaining the proper orientation and direction.

In use, the first distracting plate 24 and the second distracting plate 26 are designed to separate from a closed position, see FIG. 1, to an open or distracting position, see FIG. 2, upon activation of the distractor assembly control knob 20. The height, H (see FIG. 2) corresponds to the separation height between the distracting plates 24 and 26 required to provide the desired disc space between vertebral bodies. Rotation of the distractor assembly control knob 20 causes separation of the first distracting plate 24 and the second distracting plate 26. A locking knob 148 prevents the distractor assembly control knob 20 from rotation once in its desired position. Guiding and maintaining the distance between the first distracting plate 24 and the second distracting plate 26 are expansion members 150, 152, 154, and 156 (FIG. 4B and FIG. 5). Each of the expansion members are constructed and arranged in the same manner. As such, expansion member 150 will be described in detail with its characteristics described being applicable to the expansion members 152, 154, and 156.

The expansion member 150 is shown having an elongated body 158 having opposing ends 160 and 162. Expansion members may be arranged two per side in a crossed orientation, and are positioned so that the fit within a recessed area defined by the distractor plate side walls, tip wings, and pin guide member overhangs. Preferably, each elongated body 158 connects at one end (see end 160) to the first plate 24) and the other end (see end 162) connects to the second plate 26. Each end contains openings 164 and 166 sized to receive a pivoting device, illustrated as an expansion member pivoting rod 168 (see also FIG. 4C). The expansion member pivoting rod 168 is preferably integrally formed with or produced as a single unit, with an expansion member pivoting rod drive member, illustrated herein as an expansion member pivoting rod cylindrical drive member guiding nut 169, see FIG. 4C. The expansion member pivoting rod cylindrical drive member guiding nut 169 contains threading 171 sized and shaped to engage with threading 173 of rod 30. A retaining clip may be added at the end of rod 30 to prevent expansion member pivoting rod cylindrical drive member guiding nut 169 from moving off the rod 30. As the user manipulates knob 20, the rod 30 rotates. Rotation of the rod 30 in one direction results in the expansion member pivoting rod cylindrical drive member 169 moving axially or in a liner direction up and down the rod 30 via male/female threadings 171 and 173. As the rod 30 rotates in one direction, the pivoting rod cylindrical drive member 169 directionally moves along the rod, driving the expansion member pivoting rod 168 through the slotted region 170 positioned within each of the distractor plate side walls, causing the expansion members (150, 152, 154, 156) to move. Movement of the expansion members allows for moving of the distracting plates 24 or 26 apart, (expanded or distraction state). Rotation of the knob 20 in the opposite direction causes movement in the opposite direction, or back towards the non-expanded (non-distracted) state. Movement of the pivoting rod cylindrical drive member 169 may be accomplished by providing threading along its surface and along a portion of the surface of the rod. Other rods 171, which may be fixed in pace, may extend through opening 172 positioned within each of the distractor plate side walls. The slots 170 allow the rod to move linearly within as the plates 24 and 26 are separated or moved back together.

The expansion member pivoting rod 168 is shown using works in conjunction with works in conjunction with works in conjunction with works in conjunction with works in conjunction with two expansion members positioned on opposite sides of the distracting plates 24 and 26. For example, expansion member 150 works in conjunction with to expansion member 152 and expansion member 154 works in conjunction with expansion member 156. Opposing ends 160 and 162 each have curved or half circle surfaces 174 and 176. The having curved or half circle surfaces 174 and 176 preferably have a curvature radius, or circumference to the curvature radius or curvature radius of curved surface 178A and 178B formed in the distal tips and the curvature radius or circumference of curved surface 180A and 180B of the pin guide member 116.

In addition to having a distractor component, the cervical distractor 10 contains a centering component assembly designed to allow for proper alignment against the Uncinate Process during a surgical procedure. Referring to FIGS. 1 and 2, the centering component assembly comprises a first finger-like extension or arm 182, i.e. an elongated body extending from a portion of the cervical distractor 10, and a second finger-like extension or arm 184. The first finger-like extension 182 contains a top surface 186, a bottom surface 190, an inner surface 192, and an outer surface 194. As illustrated, the first finger-like extension 184 contains two sections, 196 and 198, which converge in a non-linear manner forming angle $\alpha$, which, for example, can be greater than 90 degrees. The second finger-like extension 184 contains a top surface 200, a bottom surface 202, an inner surface 204, and an outer surface 206. The second finger-like extension 186 contains two sections, 208 and 210, which converge in a non-linear manner forming angle $\beta$, which, for example, can be greater than 90 degrees. The first finger-like extension section 196 is orientated in a generally parallel arrangement and separated by a distance from the second finger-like extension section 208. The first finger-like extension section 198 and the second finger-like extension sections 210 are arranged in a diverging, i.e. away from the inner sleeve 17 or main body 16, orientation. As illustrated, a portion of the first finger-like extension 182 and a portion the second finger-like extension 184 are positioned about the first distracting plate 24 and the second distracting plate 26 so that sections 194 and 204 are parallel to and maintain a distance from the first distracting plate 24 and a second distracting plate 26.

The first finger-like extension 182 and the second finger-like extension 184 may be constructed and arranged to move inwardly or outwardly when the user manipulates centering component assembly control knob 22. For example, actuation of the centering component assembly control knob 22 may cause the first finger-like extension 182 and the second finger-like extension 184 to move into the lumen of the main body 16, causing a closing effect as the first finger-like extension 182 and the second finger-like extension 184 are drawn towards each other. Manipulation in the other direction moves the first finger-like extension 182 and a second finger-like extension 184 in the opposite direction. Other mechanisms of actuating the first finger-like extension 182 and the second finger-like extension 184 known to one of skill in the art may be used as well.

Figure 7:
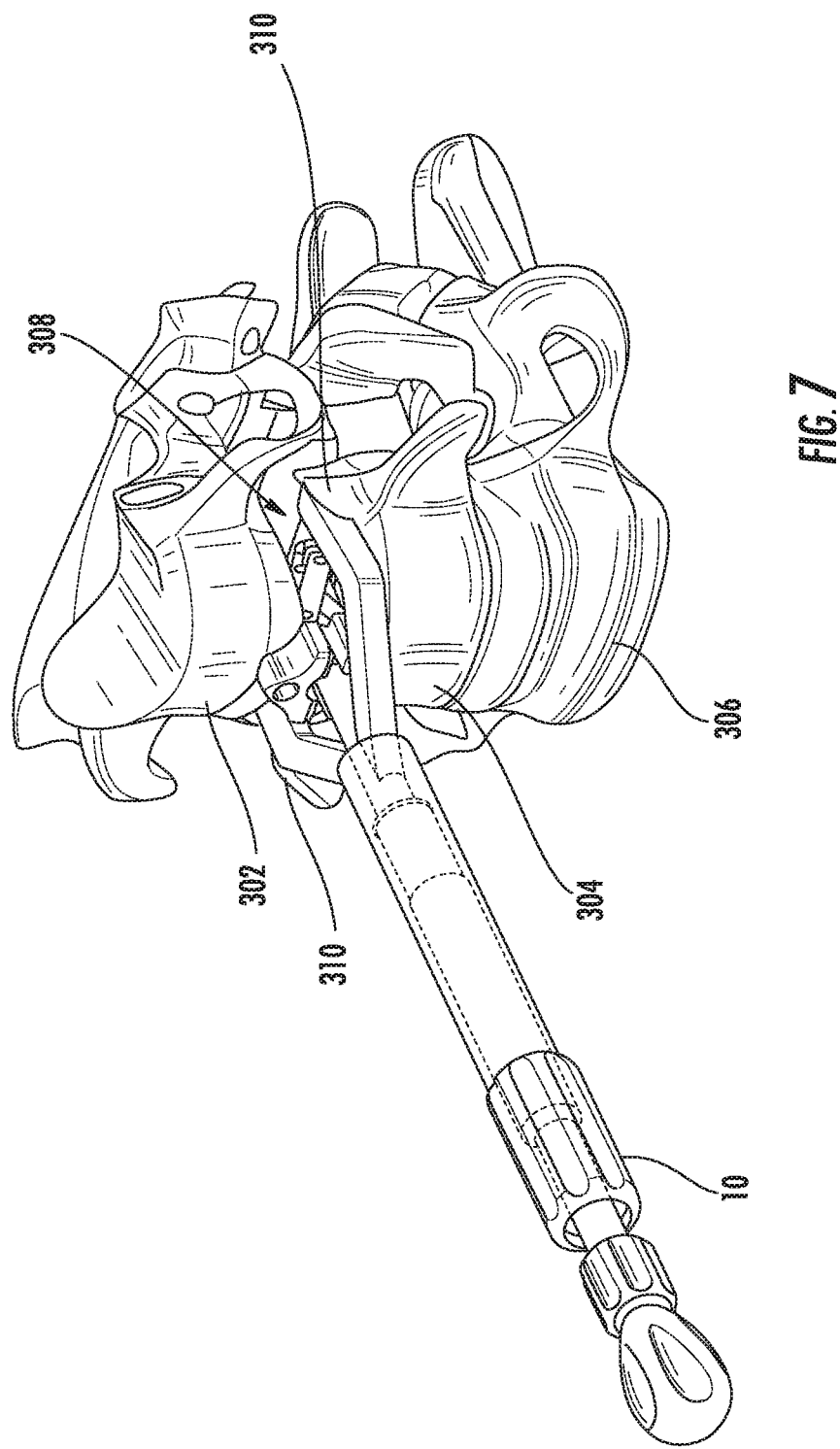
FIG. 7 is a perspective view of the cervical distractor in accordance with the present invention inserted within and distracting two cervical vertebral bodies.
Figure 8:
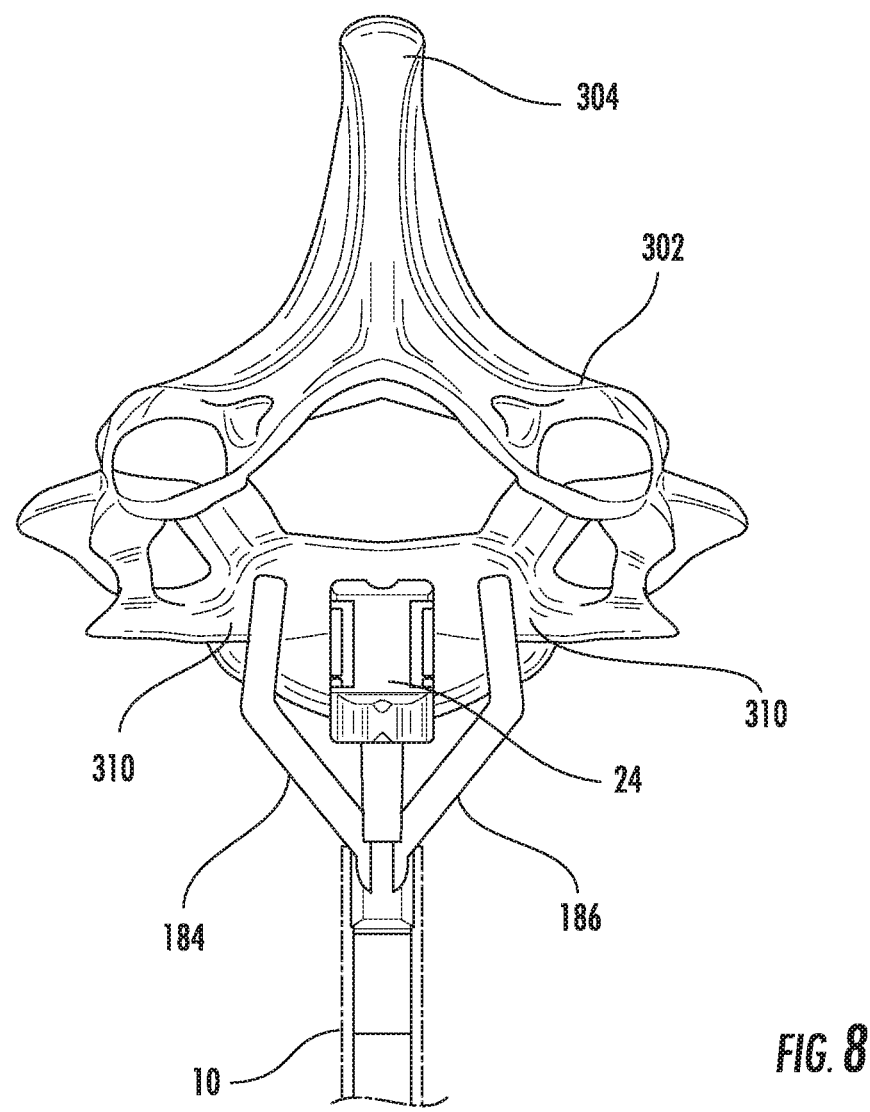
FIG. 8 is a top view of the cervical distractor in accordance with the present invention inserted within and distracting two cervical vertebral bodies.
Figure 9:
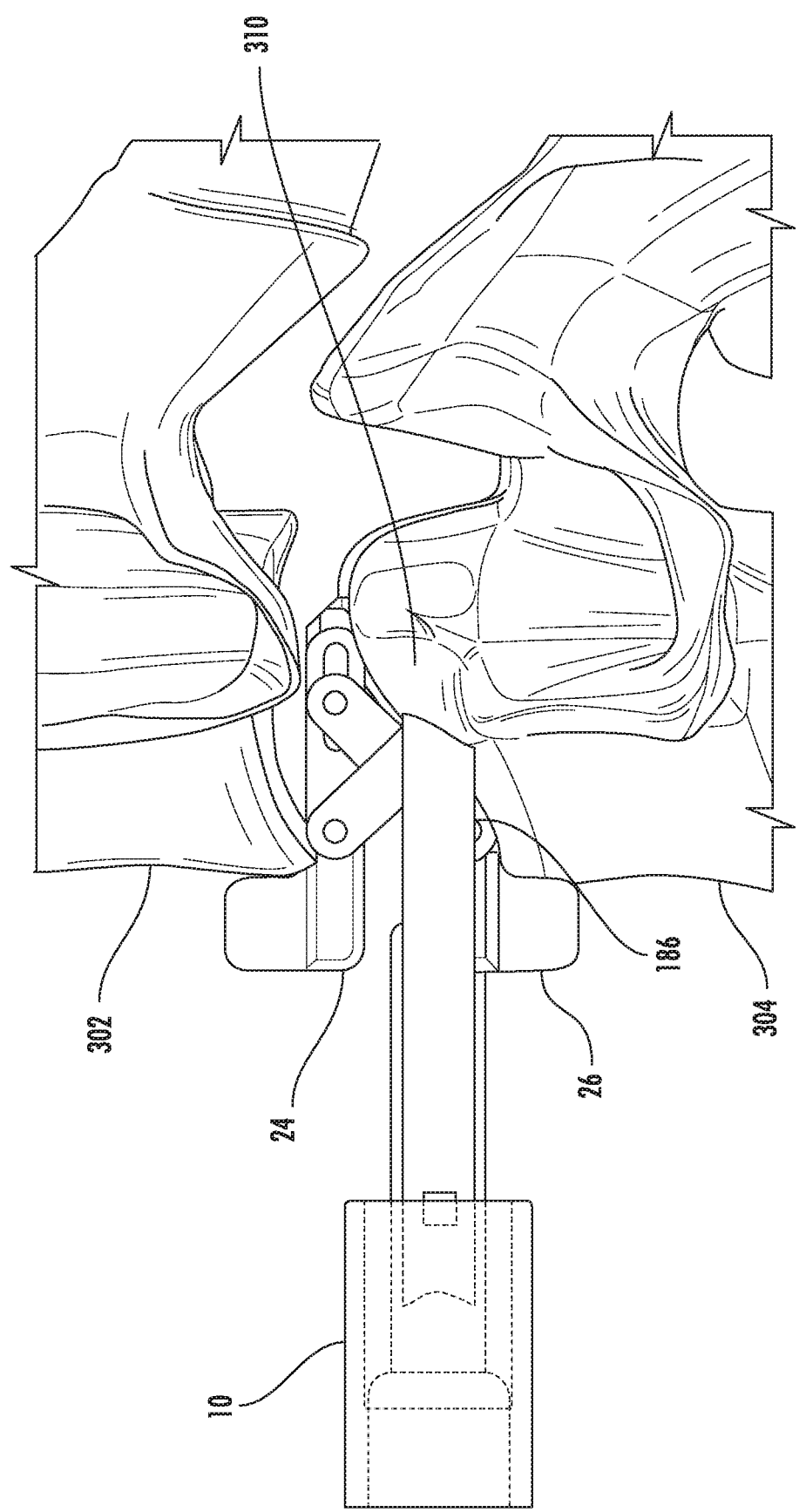
FIG. 9 is a side view of the cervical distractor in accordance with the present invention inserted within and distracting two cervical vertebral bodies.
Figure 10:
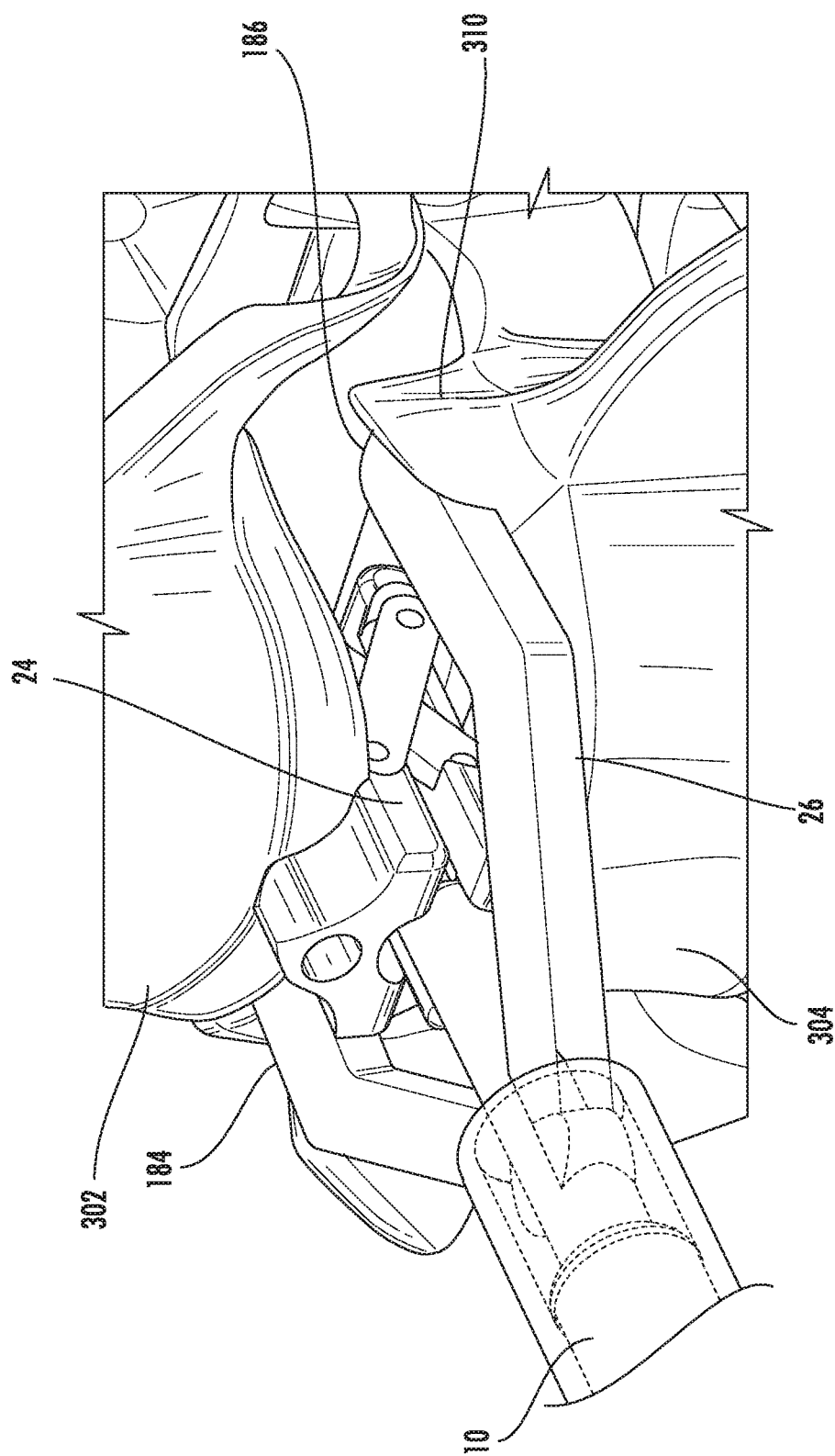
FIG. 10 is a close-up perspective view of the cervical distractor in accordance with the present invention inserted within and distracting two cervical vertebral bodies.

FIGS. 7-10 illustrate the cervical distractor 10 in use. Using techniques known to one of skill in the art, an area which requires surgical intervention is determined and accessed. Referring to FIG. 7, a partial view of cervical vertebrae is shown with cervical vertebral bodies 302, 304 and 306. The cervical distractor 10 is shown inserted within the disc space 308 between vertebral body 302 and vertebral body 304. The cervical distractor 10 is positioned so that the outer surface 194 of the first finger-like extension 182 and the outer surface 206 of the second finger-like extension 184 are moved into a position to contact the inner surface of the Uncinate Process 310, thereby centering the device against the Uncinate Process 310. The components of the distractor assembly, particularly the first distracting plate 24 and a second distracting plate 26 are inserted into the space and rest against the body surfaces of vertebral body 302 and vertebral body 304. Actuation of the distractor assembly control knob 20 causes the first distracting plate 24 and the second distracting plate 26 to distract, creating a space therebetween.

Figure 11:
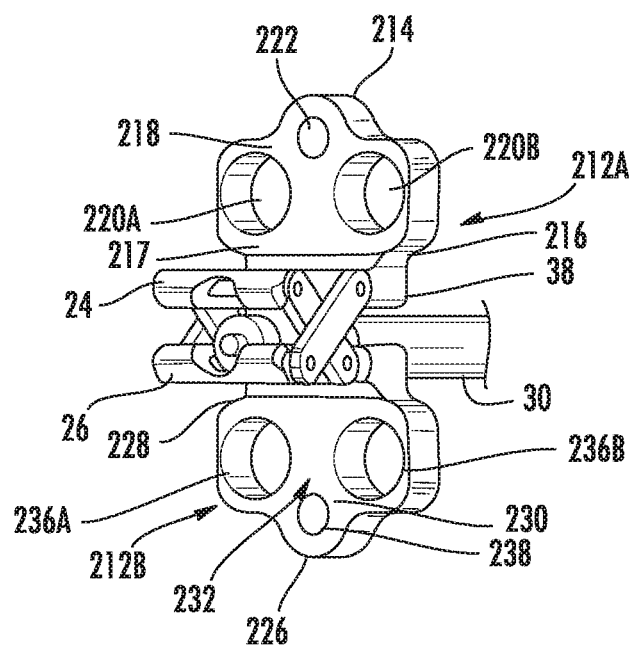
FIG. 11 illustrates the cervical distractor without several components of the centering component assembly, shown with the distracting plates having an alternative embodiment of the guide members.
Figure 12:
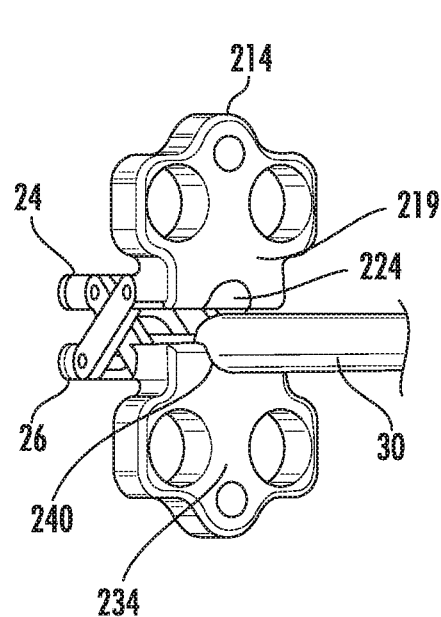
FIG. 12 is an alternative view of the cervical distractor illustrated in FIG. 11.
Figure 13:
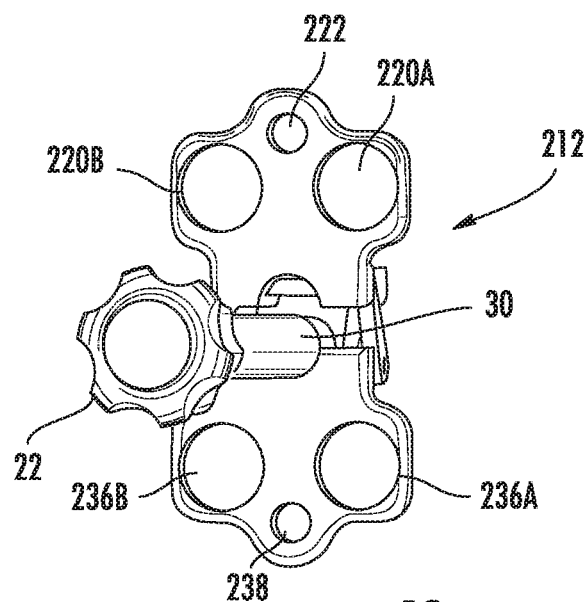
FIG. 13 is an alternative view of the cervical distractor illustrated in FIG. 11.

Referring to FIGS. 11-13, the cervical distractor 10 is shown with an alternative embodiment of a guide member, illustrated herein as guide plates 212A and 212B. The guide plate 212A is positioned at the opposing second end 38 of distracting plate 24. Preferably, the guide plate 212A is integrally formed with the distracting plate, but may be formed separately and secured thereto. The guide plate 212A has a first end 214, a second end 216 and a main body 218. The main body comprises a first surface 217 and a second opposing surface 219. Positioned within the main body 218 is a pair of openings, illustrated herein as screw guide openings 220A and 220B. The screw guide openings 220A and 220B are sized and shaped to allow the user to drill an opening for the insertion of surgical screws. Positioned above the screw guide openings 220A and 220B is a third opening, illustrated herein as a Caspar pin guide opening 222. The Caspar pin guide opening 222 is sized and shaped to receive a Caspar pin. The second surface 219 comprises a curved or semi-circular surface 224. The semi-circular surface 224 preferably has the same or similar curvature as the curvature of the distractor rod 30.

The guide plate 212B is positioned at the opposing second end 90 of distracting plate 26. Preferably, the guide plate 212B is integrally formed with the distracting plate, but may be formed separately and secured thereto. The guide plate 212B has a first end 226, a second end 228 and a main body 230. The main body 230 comprises a first surface 232 and a second opposing surface 234. Positioned within the main body 230 is a pair of openings, illustrated herein as screw guide openings 236A and 236B. The screw guide openings 236A and 236B are sized and shaped to allow the user to drill an opening for the insertion of surgical screws. Positioned above the screw guide openings 236A and 236B is a third opening, illustrated herein as a Casper pin guide opening 238. The Casper pin guide opening 238 is sized and shaped to receive a Casper pin. The second surface 234 comprises a curved or semi-circular surface 240. The semi-circular surface 240 preferably has the same or similar curvature as the curvature of the distractor rod 30.

Figure 14A:
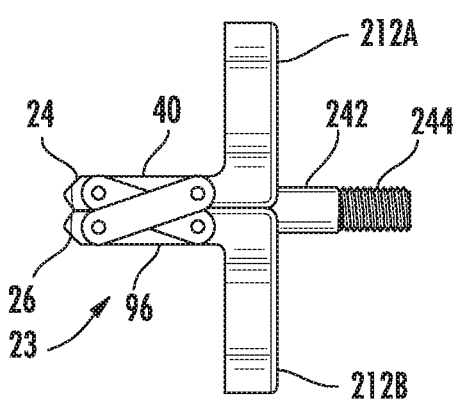
FIG. 14A is a side view of the distracting plates configured to removably engage with other portions of the cervical distractor.
Figure 15A:
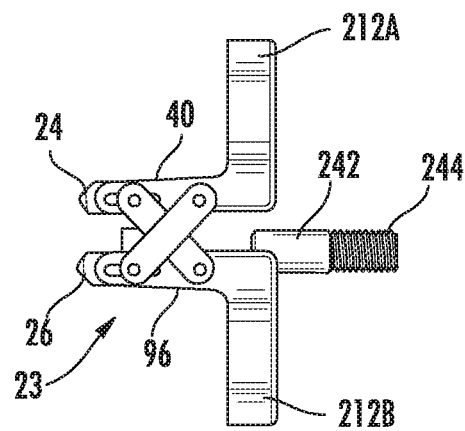
FIG. 15A is a side view of an alternative embodiment of the distracting plates configured to removably engage with FIG. 15B is a side perspective view of the distracting plates configured to removably engage with other portions of the cervical distractor illustrated in FIG. 15A.
Figure 14B:
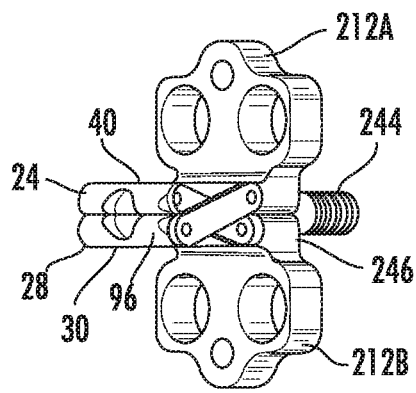
FIG. 14B is a side perspective view of the distracting plates configured to removably engage with other portions of the cervical distractor illustrated in FIG. 14A.
Figure 15B:
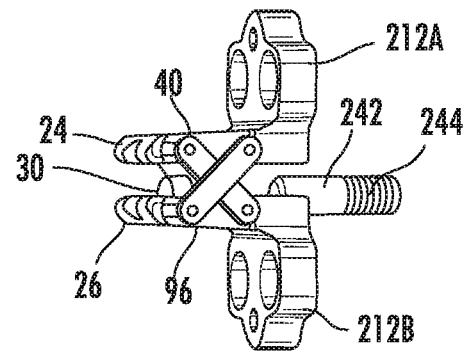

Referring to FIGS. 14A-15B, cervical distractor 10 may be designed to comprise a disposable distractor assembly 23. As shown, the distractor assembly 23 would contain the same components described in any of the embodiments previously illustrated, including the first distracting plate 24 and the second distracting plate 26, guide members (shown as 212A, 212B, but could also be 60, 116), expansion members 150, 152, 154, and 156, and a distractor rod 30. However, the distractor assembly 23 may contain an attachment member, illustrated herein as an elongated cylindrical body 242 containing external threading 244. The external threading 244 is sized and shaped to engage with internal threading within the interior of the inner sleeve 17. In this manner, a surgeon can screw the disposable distractor assembly 23 into the interior sleeve 17 of the cervical distractor 10 prior to use. After use, the surgeon can unscrew the disposable distractor assembly 23 from the interior sleeve 17 and discard. Alternatively, the attachment member may be configured to secure to the inner sleeve 17 via other mechanisms, such as by snap fitting or frictional fitting. Referring to FIGS. 14A and 14B, the first distracting plate 24 and the second distracting plate 26 are shown in a parallel arrangement. That is, the upper surface 40 of the first distracting plate 24 is parallel to the upper surface 96 of the second distracting plate 26. FIGS. 15A and 15B illustrate an alternative arrangement in which the first distracting plate 24 and the second distracting plate 26 are angled, diverging toward each other.

Figure 16C:
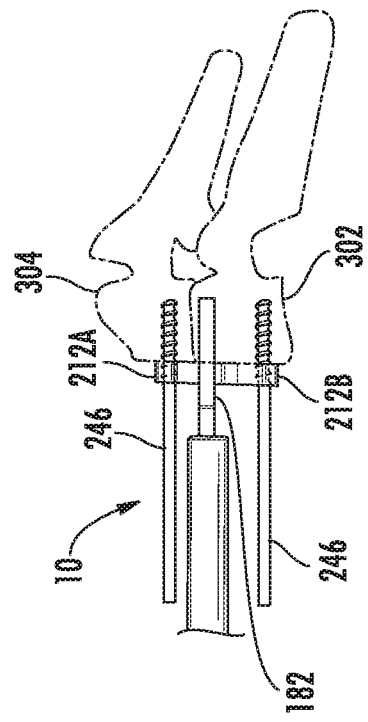
FIG. 16C is a side perspective view of the cervical distractor engaged with two vertebral bodies illustrated in FIG. 16A.
Figure 16B:
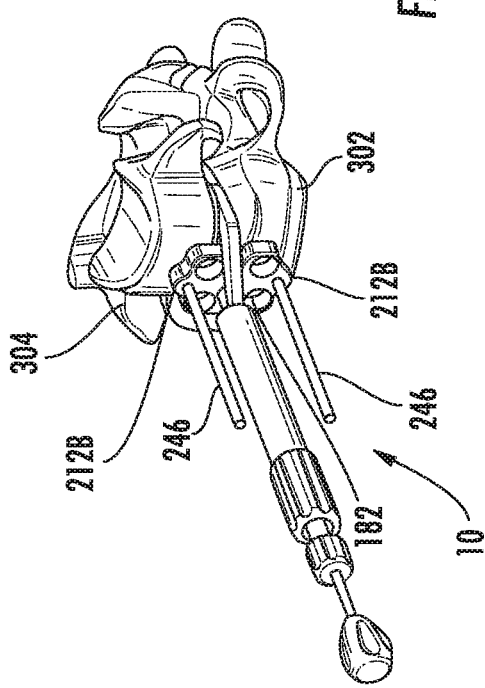
FIG. 16B is a side perspective view of the cervical distractor engaged with two vertebral bodies illustrated in FIG. 16A.
Figure 16A:
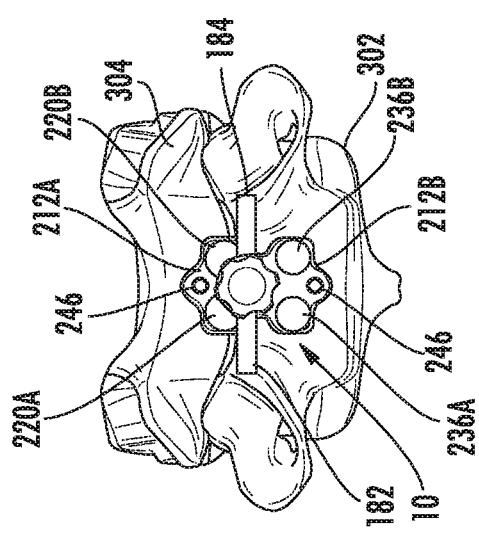
FIG. 16A is a front view of an embodiment of the cervical distractor engaged with two vertebral bodies.

Referring to FIGS. 16A-16C, the cervical distractor 10 having guide plate 212A and 212B is shown secured to cervical vertebral bodies 302 and 304 through use of Caspar pins 246. As shown in FIG. 16C, one end of the Caspar pins 246 contains a pointed and threaded end. In this position, the user can use screw guide openings 220a, 220b, 236A and 236B as a guide to drill openings for screws to be inserted into the cervical vertebral bodies 302 and 304.

Figure 17A:
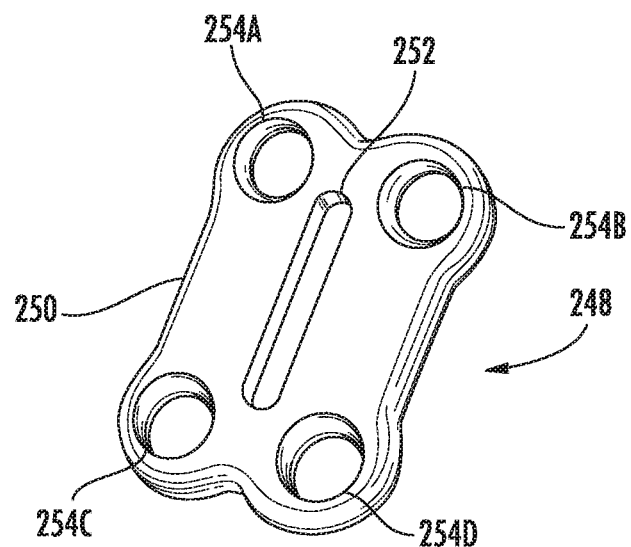
FIG. 17A shows an embodiment of a fixed cervical plate.
Figure 17B:
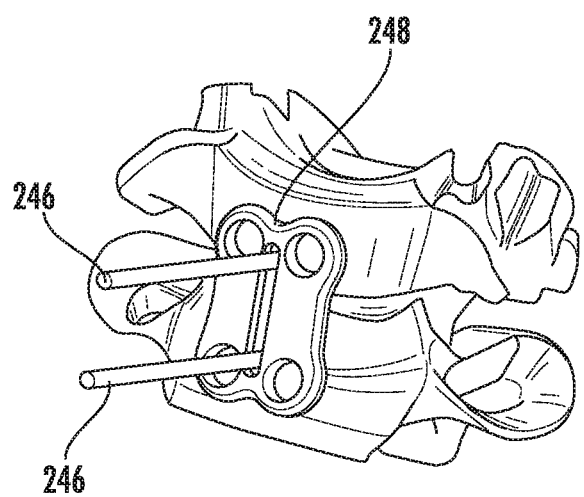
FIG. 17B illustrates the fixed cervical plate shown in FIG. 17A engaged with vertebral bodies.

FIGS. 17A and 17B illustrate embodiments of a fixed cervical plate 248. The fixed cervical plate 248 contains a main body 250 having a centrally positioned open area, illustrated herein as a slotted region 252. The slotted region 252 is sized and shaped to receive Caspar pins 246. The fixed cervical plate 248A contains a plurality of openings, 254A-D, and is referred to generally as fixed cervical plate openings 254. Each opening is sized and shaped to receive screws. The fixed cervical openings 254A and 254B are shown arranged in a parallel manner, opposite about the slotted region 252. The fixed cervical openings 254C and 254D are at the opposite end of the fixed cervical plate 248 and shown arranged in a parallel manner, opposite about the slotted region 252.

Figure 19:
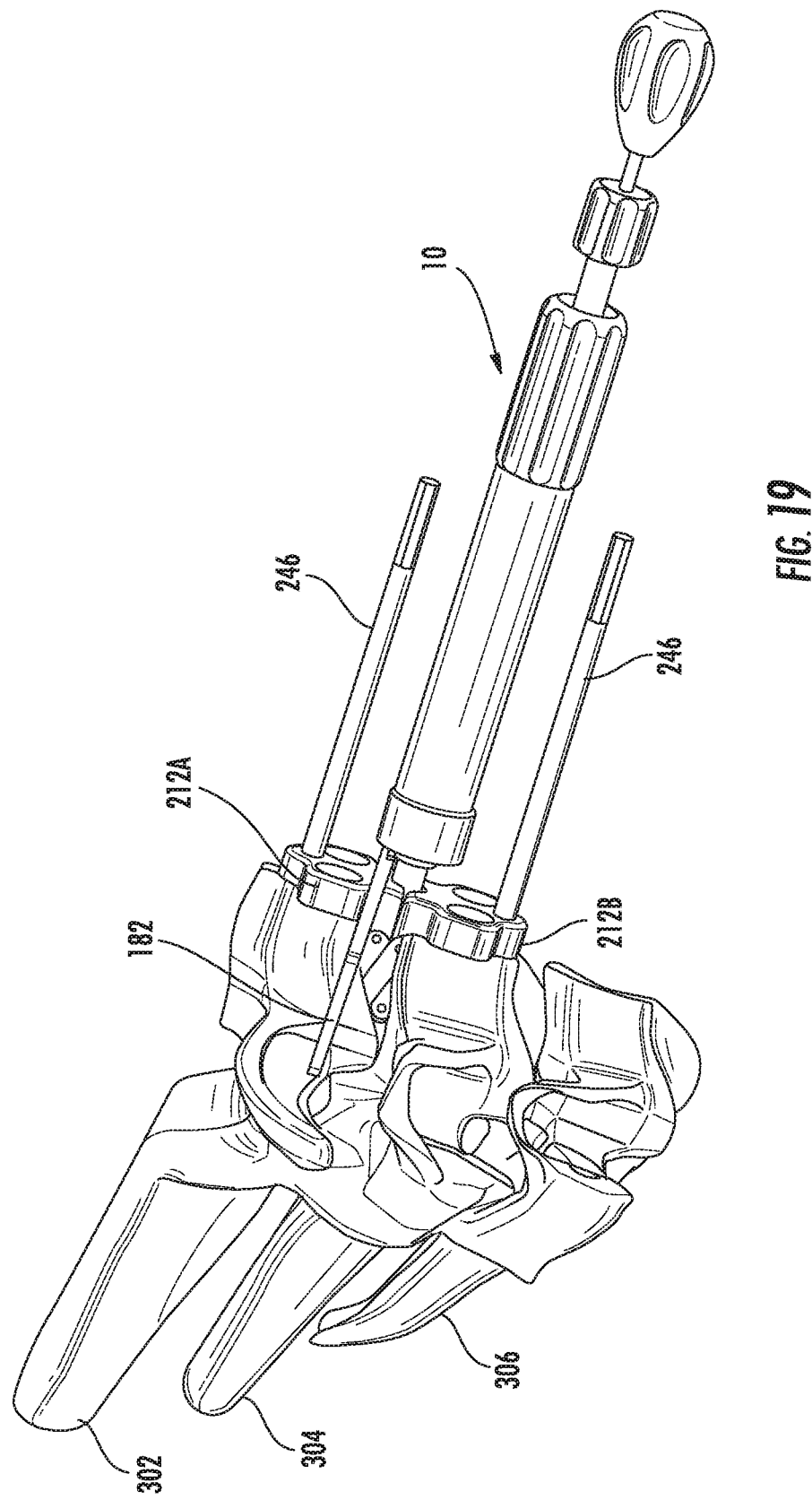
FIG. 19 illustrates the cervical distractor shown in FIG. 18 engaged with two vertebral bodies.

In use, the cervical distractor 10 is designed to provide a user the capability of centering for proper alignment and for distracting vertebral bodies. FIGS. 18-29 provide additional views for the various internal components that drive these functions. FIG. 18 illustrates an embodiment of the cervical distractor 10 having a plurality of internal components that provide for the above mentioned functionality. The cervical distractor 10 illustrated in FIG. 18 has many of the same components as described previously, with such components having the same identifying numbers. The cervical distractor is shown with the distractor assembly 23, including distracting plates 24 and 26 and the centering component assembly comprising the first finger-like extension 182 and the second finger-like extension 184. FIG. 19 illustrates the cervical distractor 10 illustrated in FIG. 18 engaged with cervical vertebral bodies 302, 304 and 306, and inserted within a disc space between vertebral body 302 and vertebral body 304. The cervical distractor 10 guide plates 212A and 212B are shown secured to cervical vertebral bodies 302 and 304 through use of Caspar pins 246.

Figure 20:
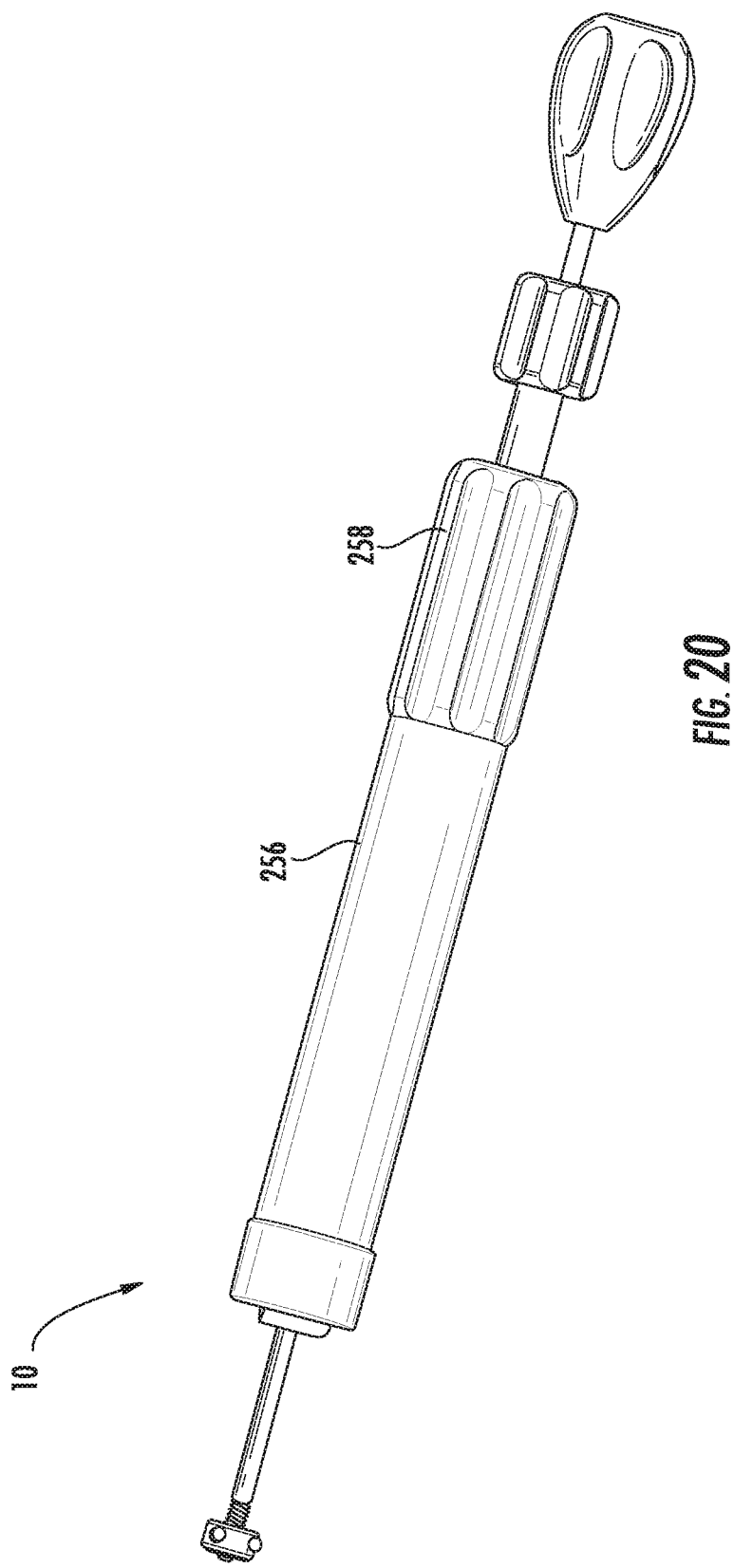
FIG. 20 is a perspective view of the cervical distractor shown in FIG. 18 with the distractor assembly and the centering component assembly removed.
Figure 21:
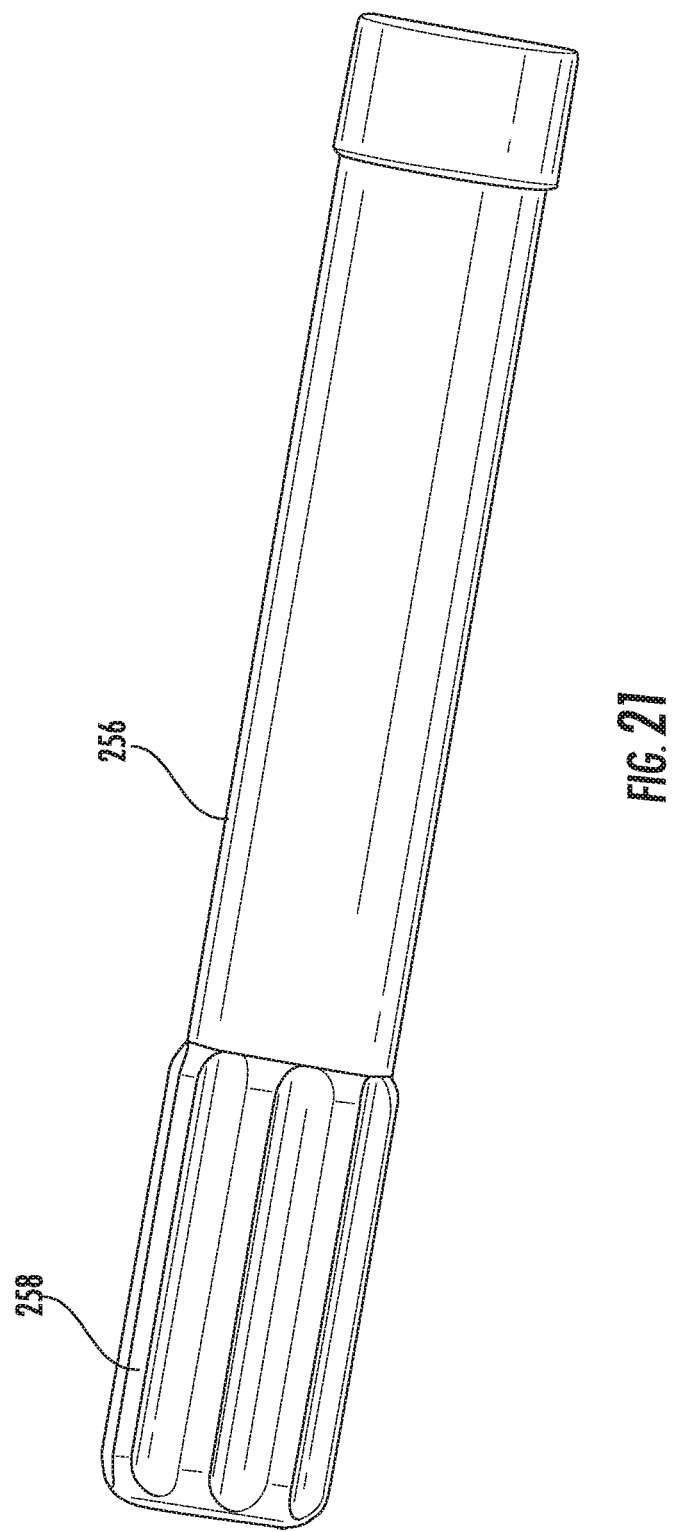
FIG. 21 is an illustrative embodiment of an outer tube shaft.
Figure 22:
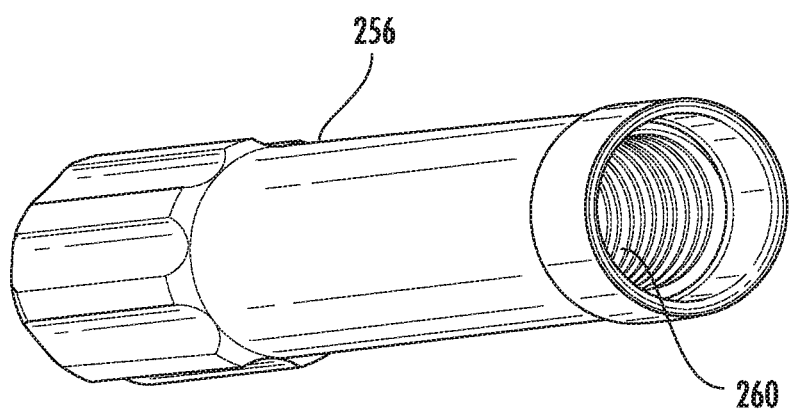
FIG. 22 is illustrates the internal threading of the outer tube shaft.
Figure 25:
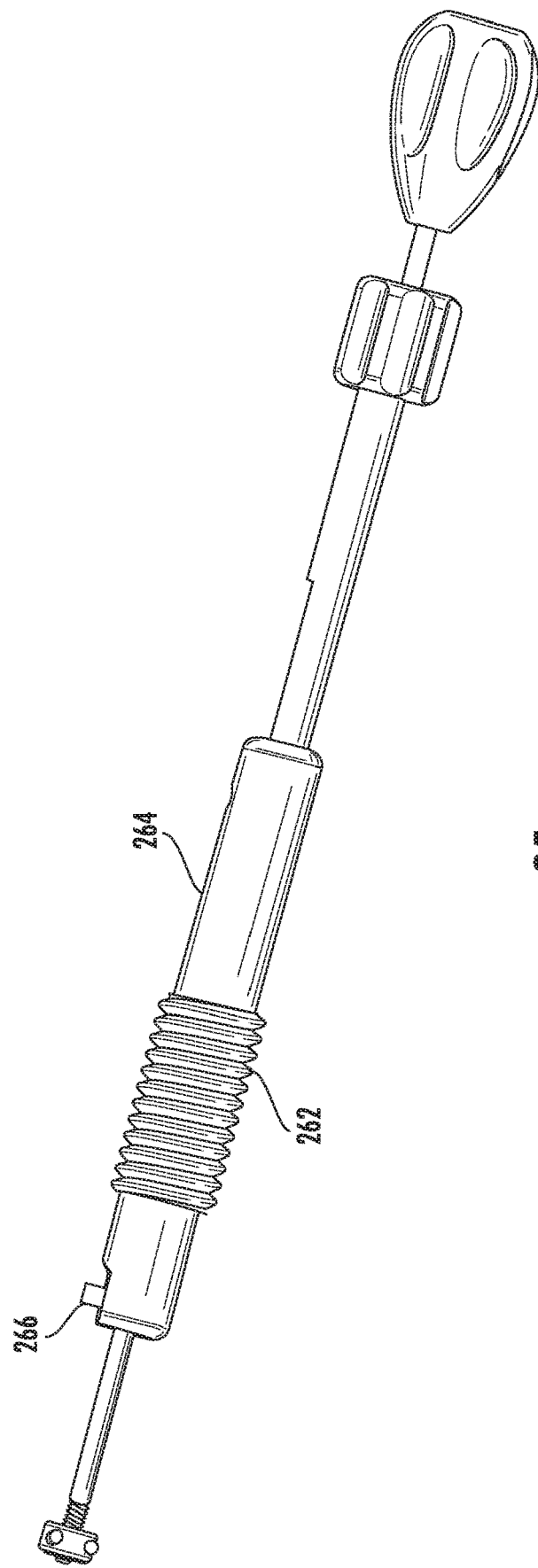
FIG. 25 is a perspective view of the cervical distractor shown in FIG. 18 with the outer tube shaft removed.
Figure 26:
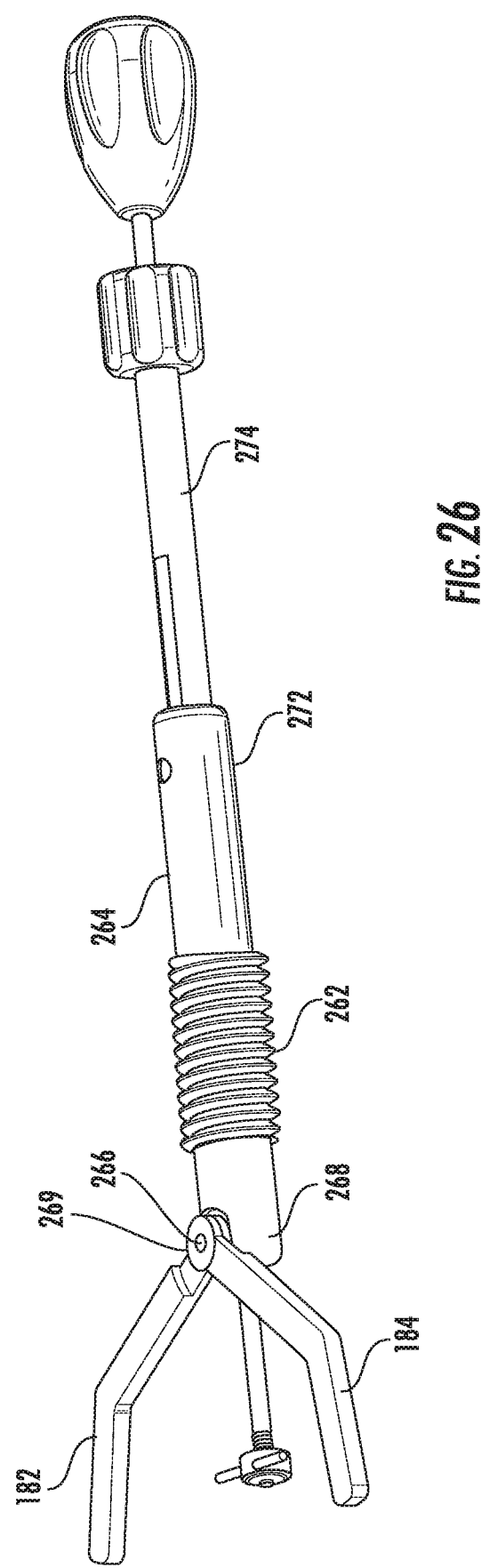
FIG. 26 is view of the cervical distractor shown in FIG. 18 with the outer tube shaft removed and showing attachment of the centering component assembly components.
Figure 27:
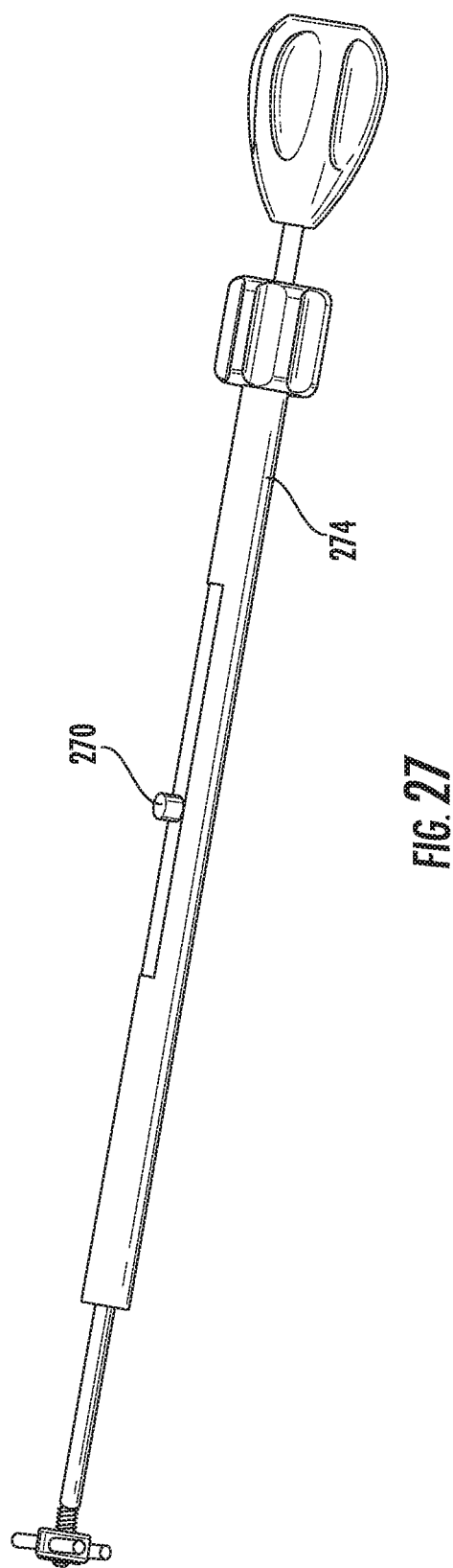
FIG. 27 perspective view of the inner sliding core shaft of the cervical distractor shown in FIG. 18.

FIG. 20 illustrates the cervical distractor 10 with distracting plates 24 and 26 and the centering component assembly first finger-like extension or arm 182 and second finger-like extension or arm 184 removed for illustration purposes. To manipulate centering component assembly first finger-like extension or arm 182 and second finger-like extension or arm 184, the user rotates the outer tube shaft 256 using grip 258. The outer tube shaft 256 has internal thread 260 (see FIG. 22) to match corresponding thread 262 of an inner sliding core shaft 264, see FIG. 25. The inner sliding core shaft 264 contains a centering component assembly finger-like extension or arm receiving member, illustrated herein as a pin 266, positioned at one (distal) end 268. The first finger-like extension or arm 182 and the second finger-like extension or arm 184 are secured to the pin 266 through opening 269 in each arm, see FIG. 26. The inner sliding core shaft 264 is prevented from spinning through the use of second pin 270 located on the proximal end 272 that hits flat on an inner holding shaft 274, see FIGS. 26 and 27. When turned, the outer tube shaft 256 moves in and out. The outer tube shaft 256 may have a bell opening distally that is configured to entrap the pivot section of the first finger-like extension or arm 182 and the second finger-like extension or arm 184, squeezing them together or allowing them to open. The first finger-like extension or arm 182 and the second finger-like extension or arm 184 may be spring loaded and kept in an open position until closed by the outer tube shaft 256. FIG. 23 illustrates the outer tube shaft 256, shown in a transparent view, in the open position, allowing the first finger-like extension or arm 182 and the second finger-like extension or arm 184 to be fully open. FIG. 24 illustrates the outer tube shaft 256, shown in a transparent view in a closed position, squeezing the first finger-like extension or arm 182 and the second finger-like extension or arm 184 to close over a portion of the cervical vertebral body.

Figure 28:
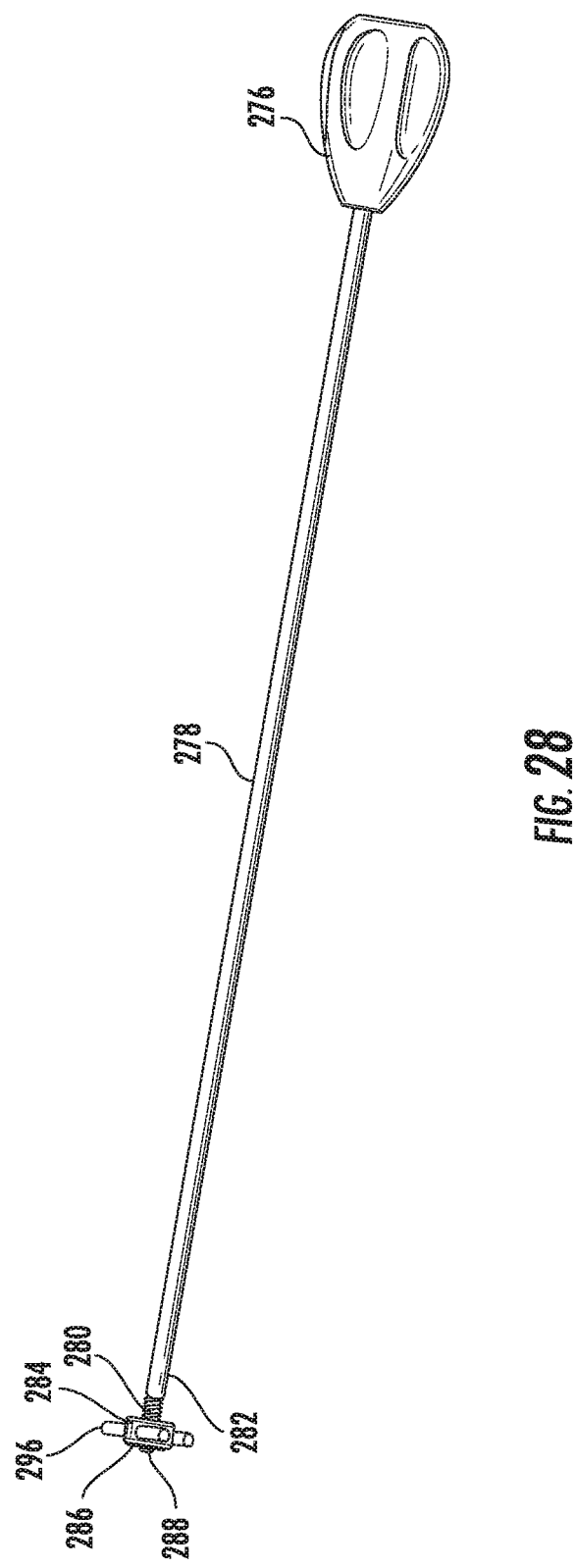
FIG. 28 is a perspective view of the central rod of the cervical distractor shown in FIG. 18.

The distraction and closure of the plates 24 and 26 is created by turning the palm handle 276 attached to a central rod 278, see FIG. 28. The central rod 278 is threaded 280 at the distal end 282 into a donut-shaped translation block 284 and captured with a c-ring 286 at the tip end 288. The transition block 284 contains arms 292, which are configured to secure to the distracting plates 24 or 26 through, for example, expansion members 150, 152, see FIG. 29. The translation block 284 is configured to slide in/out to create open-closure of the two plates 24 and 26 equally.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A distractor device comprising:
an elongated body having a first end and a second opposing end;
a plurality of distraction members positioned at or near the first end, each of said distraction members including a plurality of expansion members, said expansion members having a first end slideably engaged with a first distraction member of said plurality of distraction members and a second end fixedly engaged with a second distraction member of said plurality of distraction members;
a pair of positioning members configured to aid in positioning said elongated body in place;
a first actuating mechanism configured to actuate said pair of distracting members between a first closed position and a second distracted position; and
a second actuating mechanism configured to actuate said pair of positioning members between a first retracted and non-retracted position.

2. The distractor device according to claim 1 further including a first actuator control device engaged with said first actuating mechanism, whereby manipulation of said first actuator control device actuates movement of at least one of said plurality of distraction members.

3. The distractor device according to claim 2 further including a second actuator control device engaged with said second actuating mechanism, whereby manipulation of said second actuator control device actuates movement of at least one member of said pair of positioning members.

4. The distractor device according to claim 1 wherein said first actuating mechanism acts independently from said second actuating mechanism.

5. The distractor device according to claim 1 wherein each said plurality of distraction members contains a guide member.

6. The distractor device according to claim 5 wherein said guide member contains at least one opening.

7. The distractor device according to claim 5 wherein said guide member contains a plurality of openings.

8. The distractor device according to claim 7 wherein at least one opening is sized and shaped to receive a Caspar pin.

9. The distractor device according to claim 2 wherein said first actuating mechanism further includes a rod member, said rod member having a first end configured to aid in moving said plurality of distracting means between said open and said closed position, a second end engaged with said first actuator control device, and a main body.

10. The distractor device according to claim 9 further including a drive member coupled to said rod member.

11. The distractor device according to claim 1 wherein each said plurality of distraction members further comprises an attachment member, said attachment member sized and shaped to removably attach to a portion of said device.

12. A distractor device comprising:
a distraction assembly comprising an elongated body having a first end and a second opposing end, a plurality of distraction members positioned at or near the first end; said plurality of distraction members including at least one first distracting member and one second distracting member, said first distraction member and said second distraction member each including a plurality of expansion members, said expansion members having a first end slideably engaged with said first distraction member of said plurality of distraction members and a second end fixedly engaged with said second distraction member of said plurality of distraction members, said first distracting member and said second distracting member configured to engage with portions of adjacent vertebral bodies in a closed, non-distraction position, and when separated in an open, distracted position, provide a mechanism to move one vertebral body relative to the other adjacent vertebral body; and a distraction assembly actuating mechanism configured to actuate said distracting members between a first closed position and a second distracted position; and a centering component assembly comprising a first positioning member configured to aid in positioning said elongated body in place and a second positioning member configured to aid in positioning said elongated body in place, and a centering component assembly actuating mechanism configured to actuate said first positioning member and said second positioning member between a retracted and non-retracted position.

13. The distractor device according to claim 12 further including a first actuator control device engaged with said first actuating mechanism, whereby manipulation of said first actuator control device actuates movement of at least one of said first distracting member or said second distracting member, and a second actuator control device engaged with said second actuating mechanism, whereby manipulation of said second actuator control device actuates movement of at least one member of said pair of positioning members.

14. The distractor device according to claim 12 wherein said first distracting member and said second distracting member contains a guide member.

15. The distractor device according to claim 12 wherein at least a portion of said first positioning member and at least a portion of said second positioning member extend outwardly away from said elongated body and is positioned to maintain a distance from said first distracting member and said second distracting member.

16. The distractor device according to claim 12 wherein said first actuating mechanism further includes a rod member, said rod member having a first end configured to aid in moving said plurality of distracting means between said open and closed position, a second end engaged with said first actuator control device, and a main body.

17. The distractor device according to claim 16 further including a drive member coupled to said rod member.

18. A system for use in surgical procedures to correct spinal deformities comprising:
a distractor device comprising a distraction assembly having an elongated body having a first end and a second opposing end, a plurality of distraction members positioned at or near the first end; said plurality of distraction members including a first distracting member and a second distracting member, said first distraction member and said second distraction member each including a plurality of expansion members, said expansion members having a first end slideably engaged with said first distraction member and a second end fixedly engaged with said second distraction member, said first distracting member and said second distracting member configured to engage with portions of adjacent vertebral bodies in a closed, non-distraction position, and when separated in an open, distracted position, provide a mechanism to move one vertebral body relative to the other adjacent vertebral body; and a distraction assembly actuating mechanism configured to actuate said first and second distracting members between a first closed, non-distraction position and a second open, distracted position; and a centering component assembly comprising a plurality of positioning members configured to aid in positioning said elongated body in place, and a centering component assembly actuating mechanism configured to actuate said pair of positioning members between a first retracted and non-retracted position; and
a spinal plate having a plurality of openings to engage a plurality of bone screws.

* * * * *